(12) United States Patent
Daighighian et al.

(10) Patent No.: US 7,373,197 B2
(45) Date of Patent: May 13, 2008

(54) METHODS AND DEVICES TO EXPAND APPLICATIONS OF INTRAOPERATIVE RADIATION PROBES

(75) Inventors: Farhad Daighighian, Santa Monica, CA (US); Henry M. Daghighian, Huntington Beach, CA (US); Barry Leon, West Homstead, NY (US)

(73) Assignee: Intramedical Imaging, LLC, Los Angeles, CA (US)

( * ) Notice: Subject to any disclaimer, the term of this patent is extended or adjusted under 35 U.S.C. 154(b) by 1043 days.

(21) Appl. No.: 10/190,113

(22) Filed: Jul. 3, 2002

(65) Prior Publication Data

US 2002/0168317 A1 Nov. 14, 2002

Related U.S. Application Data

(63) Continuation-in-part of application No. 09/518,457, filed on Mar. 3, 2000, now Pat. No. 6,602,488.

(60) Provisional application No. 60/303,329, filed on Jul. 5, 2001.

(51) Int. Cl.
*A61B 6/00* (2006.01)
*G01T 1/24* (2006.01)
(52) U.S. Cl. .................. 600/436; 250/370.11
(58) Field of Classification Search ............... 600/407, 600/411, 427, 436, 476–478; 250/370.11, 250/370.12, 370.15; 378/6, 165, 210
See application file for complete search history.

(56) References Cited

U.S. PATENT DOCUMENTS 3,112,402 A 11/1963 Okun et al.

(Continued)

FOREIGN PATENT DOCUMENTS

WO WO9503083 2/1995

(Continued)

OTHER PUBLICATIONS

Barber et al, University of Arizona, *IEEE Transactions on Nuclear Science*, vol. ns-27, No. 1 Feb. 1980, *Small Radiation Detectors for Bronchoscopic Tumor Localization* pp. 496-502.

(Continued)

*Primary Examiner*—Francis J. Jaworski
(74) *Attorney, Agent, or Firm*—Koppel, Patrick, Heybl & Dawson; Michael J. Ram

(57) ABSTRACT

Labeling, such as with radio pharmaceuticals, fluorescence emitting compounds or other probe detectable materials, of diseased or malfunctioning candidate cells for subsequent treatment with a medicinal compound, the identification in situ of the candidate cells using a probe sensitive to the presence of the label and then treatment of the identified cell is disclosed.

The invention also covers in situ gene therapy using a beta or gamma radiation detection probe to locate radio-labeled cells, and the delivery of corrective or therapeutic genes to the candidate cells identified by the radiation detection probe while the probe is positioned adjacent to the labeled and located cells. Also covered is the identification of vulnerable plaque in atherosclerotic vessels and diseased myocardial tissue in the heart, treatment of that plaque or diseased tissue and the subsequent determination of the efficacy of the treatment.

Devices for use in the procedures include, intraoperative radiation detection probes, intraoperative radiation detection probes, intraoperative radiation imaging probes, catheter mounted radiation detection probes and probes attached to surgical gloves so that the probe tip can be manually manipulated by the physician and placed adjacent to suspect tissue at an operative site.

20 Claims, 10 Drawing Sheets

U.S. PATENT DOCUMENTS

| | | | |
|---|---|---|---|
| 3,310,675 A | 3/1967 | Prickett et al. | |
| 3,427,454 A | 2/1969 | Webb | |
| 3,598,109 A | 8/1971 | Kobayashi et al. | |
| 3,609,370 A | 9/1971 | Peyser | |
| 3,628,021 A | 12/1971 | MacDonald | |
| 3,670,719 A | 6/1972 | Kobayashi et al. | |
| 3,863,623 A | 2/1975 | Trueblood et al. | |
| 3,869,615 A | 3/1975 | Hoover et al. | |
| 3,919,589 A | 11/1975 | Stevens | |
| 3,936,646 A | 2/1976 | Jonker | |
| 4,340,818 A | 7/1982 | Barnes | |
| 4,419,585 A | 12/1983 | Strauss et al. | |
| 4,489,426 A | 12/1984 | Grass et al. | |
| 4,502,147 A | 2/1985 | Michaels | |
| 4,595,014 A | 6/1986 | Barrett et al. | |
| 4,782,840 A | 11/1988 | Martin, Jr. et al. | |
| 4,801,803 A | 1/1989 | Denen et al. | |
| 4,932,412 A | 6/1990 | Goldenberg | |
| 4,959,547 A | 9/1990 | Carroll et al. | |
| 4,976,266 A | 12/1990 | Huffman et al. | |
| 4,995,396 A | 2/1991 | Inaba et al. | |
| 5,008,546 A | 4/1991 | Mazziotta et al. | |
| 5,014,708 A | 5/1991 | Hayashi et al. | |
| 5,036,201 A | 7/1991 | Carroll et al. | |
| 5,042,486 A | 8/1991 | Pfeiler et al. | |
| 5,088,492 A * | 2/1992 | Takayama et al. | 600/431 |
| 5,151,598 A | 9/1992 | Denen | |
| 5,170,055 A | 12/1992 | Carroll et al. | |
| 5,275,166 A | 1/1994 | Vaitekunas et al. | |
| 5,313,065 A | 5/1994 | Reed | |
| 5,325,855 A | 7/1994 | Daghighian et al. | |
| 5,331,961 A | 7/1994 | Inaba et al. | |
| 5,338,937 A | 8/1994 | Daghighian et al. | |
| 5,383,456 A | 1/1995 | Arnold et al. | |
| 5,424,546 A | 6/1995 | Okada et al. | |
| 5,441,050 A | 8/1995 | Thurston et al. | |
| 5,444,254 A | 8/1995 | Thomson | |
| 5,471,988 A | 12/1995 | Fujio et al. | |
| 5,485,846 A | 1/1996 | Webler et al. | |
| 5,635,717 A | 6/1997 | Popescu | |
| 5,657,759 A | 8/1997 | Essen-Moller | |
| 5,682,888 A | 11/1997 | Olsen et al. | |
| 5,702,384 A | 12/1997 | Umeyama et al. | |
| 5,703,056 A | 12/1997 | Blasberg et al. | |
| 5,776,064 A | 7/1998 | Kalfas et al. | |
| 5,811,814 A * | 9/1998 | Leone et al. | 250/368 |
| 5,814,295 A | 9/1998 | Martin, Jr. et al. | |
| 5,846,513 A | 12/1998 | Carroll et al. | |
| 5,857,463 A | 1/1999 | Thurston et al. | |
| 5,899,860 A | 5/1999 | Pfeiffer et al. | |
| 5,938,605 A * | 8/1999 | Hasing et al. | 600/436 |
| 5,961,458 A | 10/1999 | Carroll | |
| 6,119,031 A * | 9/2000 | Crowley | 600/407 |
| 6,295,680 B1 * | 10/2001 | Wahl et al. | 600/431 |
| 6,510,336 B1 * | 1/2003 | Daghighian et al. | 600/427 |
| 2002/0001608 A1 * | 1/2002 | Polson et al. | 424/426 |

FOREIGN PATENT DOCUMENTS

WO     WO9703369     1/1997

OTHER PUBLICATIONS

Woolfenden et al, *Lung Cancer Detection Using a Miniature Sodium Lodide Detector and Cobalt—57 Bleomycin*, Chest-85, 1, Jan., 1984, pp. 84-88.

\* cited by examiner

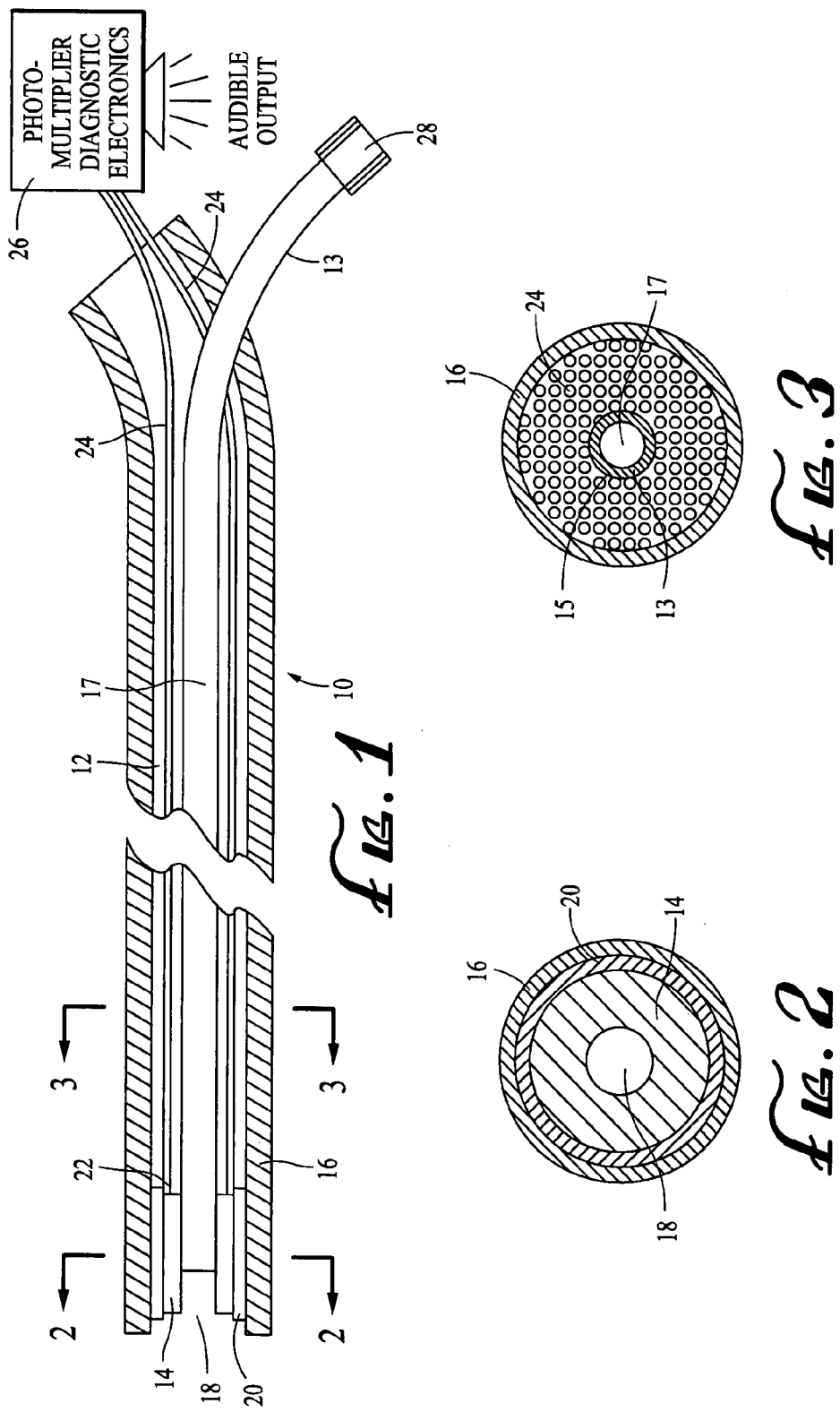

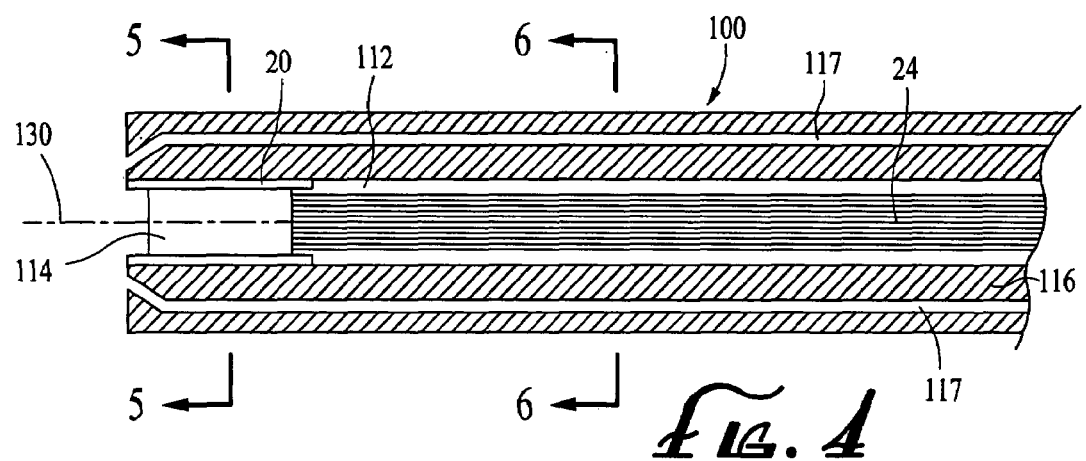
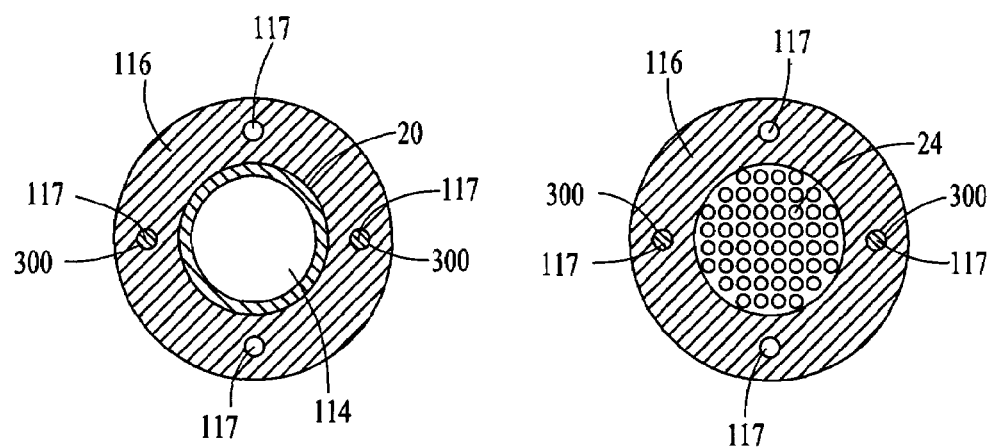

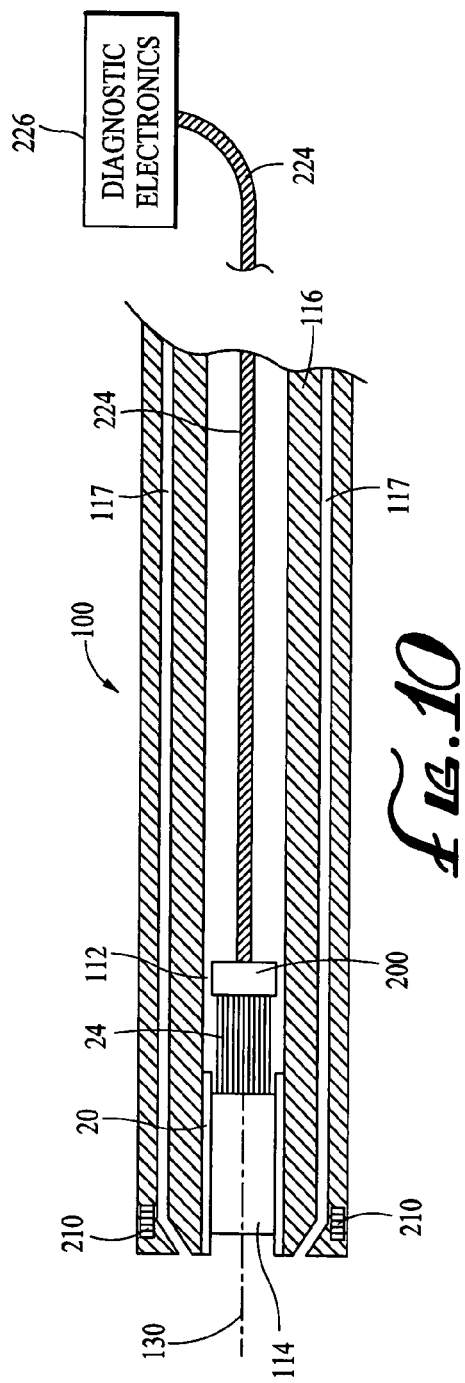
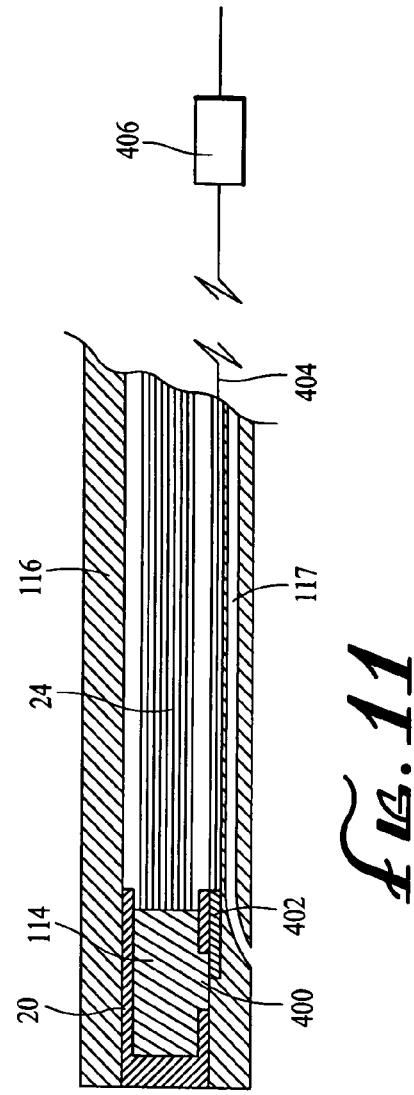

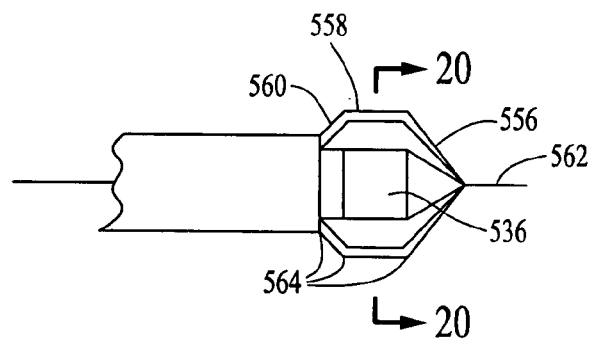
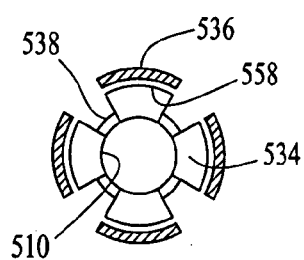
*fig.* 19    *fig.* 20
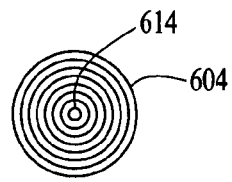
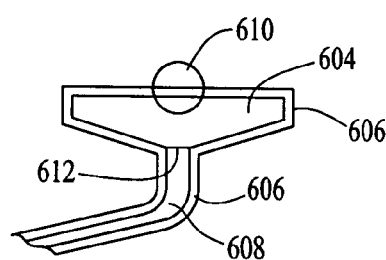
*fig.* 22    *fig.* 23
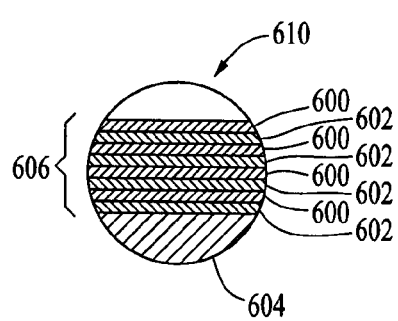
*fig.* 24

METHODS AND DEVICES TO EXPAND APPLICATIONS OF INTRAOPERATIVE RADIATION PROBES

This application is a continuation-in-part of U.S. Ser. No. 09/518,457 filed Mar. 3, 2000 now U.S. Pat. No. 6,602,488 and incorporates the disclosures set forth, under the Disclosure Document Program, Ser. No. 489,310 filed Feb. 26, 2001, the Disclosure Document filed Mar. 12, 2001 entitled "METHODS AND DEVICES TO EXPAND APPLICATIONS OF INTRAOPERATIVE RADIATION PROBES" and Disclosure Document, Ser. No. 491,121, filed Mar. 21, 2001 and claims benefit of Provisional Patent Application 60/303,329 filed Jul. 5, 2001.

BACKGROUND OF THE INVENTION

The invention relates to the labeling, such as with radio pharmaceuticals, fluorescence emitting compounds or other probe detectable materials, of diseased or malfunctioning candidate cells for subsequent treatment with a medicinal compound, the identification in situ of the candidate cells using a probe sensitive to the presence of the label and then treatment of the identified cell. Alternatively, normal tissue may be label such that diseased tissue appears as a cold (unlabeled) spot. Still further, certain tissue may be labeled with a certain radioisotope or fluorescing compound while other tissue is labeled with a different detectable material so the different tissue provides a different emission, i.e. beta versus gamma radiating radioisotopes, or two radioisotopes emitting gamma rays with different energies or radiation versus florescence emissions. A further variation involves using a radiolabeled treatment medium which is applied to labeled or unlabeled tissue. The efficacy of the delivery technique and treatment effectiveness can then be monitored. If labeled treatment medium is delivered to labeled tissue, it is preferred that different radioisotope, fluorescence or otherwise detectable material be used for labeling the tissue and treatment medium. However, the same labeling material can be used and effectiveness determined based on the enhancement of the radiation count from the target tissue. While the inventions described below are primarily discussed using radiolabeling in conjunction with suitable radiation detectors, other labeling, such as fluorescence labeling with optical sensors can be used as alternate approaches. One skilled in the art will recognize that other detectable labeling and suitable detection probes can be used in the inventive devices and procedures described herein.

Addressed are improved instruments with enhanced operability, controllability, diagnostic capability and treatment capability. For example, the described devices can be used in an MRI environment, can provide a visual image as well as a radiation image, allow 3D tracking of the probe's position and direction correlating with tomographic images taken before surgery, provide a controllable field of view, and allow delivery of treatment compounds which themselves may be radiolabeled, which may have probe detectable labels, to the disease tissue rather than surrounding normal tissue, or vice versa, while the probe is at the site of the labeled cells. A determination can then be made as to whether the treatment compounds have in fact been incorporated into the target tissue. Subsequent diagnostic use of the probes at the same body site can also determine if the diseased tissue has been replaced in whole or in part by normal tissue as well as the extend of replacement or healing at the treatment site.

In one embodiment, the invention relates to in situ gene therapy using a beta or gamma radiation detection probe to locate radio-labeled cells, also referred to as candidate cells, and the delivery of corrective or therapeutic genes to the candidate cells identified by the radiation detection probe while the probe is positioned adjacent to the labeled and located cells. Other treatment modalities involve the identification of vulnerable plaque in atherosclerotic vessels, treatment of that plaque and the subsequent determination of the efficacy of the treatment. A still further treatment modality involves the location of diseased myocardial tissue in the heart using specific radiotracers, delivery of a treatment composition directly to that tissue and the subsequent evaluation of efficacy of that treatment.

Devices for use in the procedures contemplated by the invention herein include, but are not limited to, intraoperative radiation detection probes, intraoperative radiation imaging probes, catheter mounted radiation detection probes and probes attached to surgical gloves so that the probe tip can be manually manipulated by the physician and placed adjacent to suspect tissue at an operative site. These probes carry one or more radiation detectors. This includes the use of different detectors (i.e. gamma and beta detectors) on a single probe or the use of two different probes delivered simultaneously or serially to the targeted site. Reference to radiation is not limited to nuclear radiation but also includes optical radiation (fluorescence, phosphorescence, including UV, visible or IR emissions) and related detectors and transmission devices.

DESCRIPTION OF THE PRIOR ART

Most of the basic elements of biological materials have radiation emitting isotopes (e.g., C-11, N-13, O-15, F-18, I-124). For example, these compounds can be labeled with isotopes which emit electrons or positrons (collectively known as beta rays) or gamma rays. More than 500 biochemicals have been labeled with these isotopes (e.g., amino acids, fatty acids, sugars, antibodies, drugs, neuroreceptor peptides, neuroreceptor ligands, nucleoside analogues, etc).

Recently, several chemical compounds have been labeled with various positron emitting tracer isotopes for the imaging of gene expression. For example I-124 labeled FIAU a 2'-fluoro-substituted nucleotide analogue, and PET studies performed on rats (Tjuvajev et al. Cancer Res 55, 6126-6132 (1995); Tjuvajev et al. Cancer Res 56, 4087-4095 (1996); Tjuvajev et al. Cancer Res.(1999)in Press) [8-$F^{18}$]-fluoroganciclovir has been used for PET studies of gene transduction in mice (Gambhir et al. J. Nucl. Med. (1998); Haberkorn U et al. J Nucl. Med. 38: 1048-1054 (1997)), U.S. Pat. No. 5,703,056 to Blasberg et al. The goal of these procedures was to introduce radiolabeled tracers after gene therapy to determine if the gene therapy was successful.

The new method described in this patent application is fundamentally different because radiolabeled tracers are used to locate the cells that are suitable candidates for gene therapy before the therapy is applied.

Goldbenberg, et al., accomplished more specific labeling by the use of $I^{131}$-labelled heterologous (goat) antibodies to human carcinoembryonic antigen (CEA). (Goldenberg, D. M.: "Oncofetal and other Tumor-associated Antigens of the Human Digestive System", *Curr. Top. Pathol.* 63: 289-342, 1976. Goldenberg, D. M.; Deland, F.; Kim, E. E.: "Human Chorionic Gonadotrophin Radioantibodies in the Radioimmunodetection of Cancer and the Disclosure of Occult Metastases" *Proc. Nat'l. Acad. Sci.* 78: 7754-7758, 1981. Goldenberg, D. M.; Deland, F.; Kim, E. E., et al.: "Use of Radiolabeled Antibodies to Carcinoembryonic Antigen for the Detection and Localization of Diverse Cancers by External Photoscanning", *N. Engl. J. Med.* 298: 1384-1388, 1978; Goldenberg, D. M.; Preston, D. F.; Primus, F. J.; Hansen, H. J.: "Photoscan Localization of GW-39 Tumors in Hamsters Using Radiolabeled Anticarcinoembryonic Antigen Immunoglobulin" *J. Cancer Res.* 34: 1-9, 1974; Goldenberg, D. M.; Sharkey, R. M.; Primus, F. J.: "Carcinoembryonic Antigen in Histopathology: Immunoperoxidase Staining of Conventional Tissue Sections", *J. Natl. Cancer Inst.* 57: 11-22, 1976.) CEA is a tumor-associated antigen of gastrointestinal cancer, particularly colon and pancreatic cancer, first described by Gold. (Gold, P., Freedman, S. O.: "Demonstration of Tumor Specific Antigen in Human Colonic Carcinomata by Immunologic Tolerance and Absorption Techniques", *J. Exp. Med.* 121: 439-462, 1965.) Other labeled antibodies usable for tagging tumor cells include monoclonal antibody 17-1A and its $F(ab')_2$ fragment (Wistar Institute, Philadelphia, Pa.), monoclonal antibody 19-9 and its $F(ab')_2$ fragment (Centocor, Inc., Philadelphia, Pa.), monoclonal antibody B72.3 (Dr. Jeffrey Schlom, National Cancer Institute) and CC49 and CC83, both second generation B72.3 antibodies. These are identified as examples of suitable materials and are not meant to limit the scope of compounds usable to label cells. Many other compounds, such as single chained antibodies (SCAs) disclosed in U.S. Pat. No. 4,946,778, capable of labeling specific cells, are identified in the literature and are constantly being discovered and/or developed. Labeling nucleotides detectable by a gamma probe include technetium $Tc^{99}$, iodine $I^{123}$, $I^{125}$, and $I^{131}$, indium $In^{111}$, selenium $Se^{75}$, and cobalt $Co^{57}$. These and other radioisotopes can be detected by beta or gamma probes.

Martin et al., U.S. Pat. No. 4,782,840, incorporated herein by reference, describes a procedure which requires the administration of $I^{125}$ labeled antibody or antibody fragments to a patient to label cancerous tissue. Some time after administration (2 to 21 days) the suspected site is accessed surgically and, using a hand-held gamma probe, the labeled tissue is located and surgically removed.

Applicant is a coinventor on U.S. Pat. Nos. 5,008,546, 5,325,855 and 5,338,937 which describe and claim variations to prior known intraoperative radiation probes. Others describe the use of gamma probes as a biopsy probe for locating, localizing or mapping tagged tissue located throughout the body and particularly near the liver, kidney, or blood vessels or to localize lymph nodes (U.S. Pat. Nos. 4,959,547, 5,170,055 and 5,036,201 to Carroll et al; U.S. Pat. No. 5,383,456 to Arnold et al.). Leone et al, U.S. Pat. No. 5,811,814 describes a catheter, including fiber optics and a scintillation crystal, suitable for locating concentrations of alpha, beta, gamma or X-ray labeled compounds introduced into the arteries and veins. The Leone device includes a radiation blocking member adjacent one of the distal and proximal ends of the scintillator. The purpose of the blocking member is to block photons emitted by sources of radiation in front of or behind the scintillation material so that sources of radiation in axial alignment with a major or longitudinal axis of the scintillation material will not, for the most part, be detected or measured. As a result, only photons traveling along paths that intersect the side wall of the scintillation material will impact the scintillation material and be detected.

The use of radiation detection probes placed through scopes to locate radionuclide labeled tissue has been described in the literature for many years. Both Barber et al and Woolfenden et al. described the insertion of a gamma ray detection probe through an open channel in a broncoscope. (Barber, H. B., Woolfenden, J. M., Donahue, D. J., Nevin, W. S., "Small Radiation Detectors for Bronchoscopic Tumor Localization", *IEEE Transactions on Nuclear Science*, NS-27, No. 1 February 1980; Woolfenden, J. M., Nevin, W. S., Barber, H. B., Donahue, D. J., "Lung Cancer Detection Using a Miniature Sodium Iodide Detector and Cobalt-57 Bleomycin", *Chest,* 85, Jan. 1, 1984). Goldenberg, U.S. Pat. No. 4,932,412, issued Jun. 12, 1990 claimed the same technique. Also, Carol's method requires removal of the probe before a treatment instrument can be inserted. In contrast, the invention described herein requiresthat the probe be present and so that the radio-labeled tissue can be targeted and treated.

U.S. Pat. No. 5,846,513 to Carroll et al. describes a probe for percutaneous insertion into a body through a delivery sheath followed by the removal of the probe and insertion through the same sheath of an instrument, such as a resectoscope, to remove the identified tissue. Alternatively, the '513 patent discloses that, following removal of the probe, other tumor destroying techniques can be practiced by delivering a treatment media or device through the sheath, such as cancer cell necrotizing agents, high intensity ultrasound, microwave energy, laser energy, heat electrocoagulation, or the introduction of tumor destructive chemical agents such as free radical promoters, copper or iron ions, oxidants, iodine, tissue digestive enzymes, alcohol or radioactive seeds. However, Carroll et al did not suggest the delivery of compositions for gene therapy which, as discussed below, function in a fundamentally different manner from chemical, mechanical or electrical tumor destruction techniques. Also, Carroll's method requires removal of the probe before a treatment instrument can be inserted. In contrast the invention described herein requires that the probe be present so that the radio-labeled tissue can be targeted and treated.

U.S. Pat. Nos. 5,453,609 ; 5,568,532 and 5,864,141 show further designs for probes containing scintillators and photomultiplier tubes connected thereto.

U.S. Pat. No. 5,014,708 discloses a device insertable within the body, which includes in combination, a radiation sensing probe with an ultrasonic tip and aspiration function to remove tissue released by the vibrating ultrasound tip. U.S. Pat. No. 4,995,396 sets forth an endoscope which includes, in combination, a radiation detecting probe with means to deliver tumor affinable chemicals which can then be activated by laser light transmitted through fiber optics (photodynamic therapy) also enclosed within the endoscope. Neither patent suggests gene therapy or the other new functions described below.

Raylman and Wahl disclose beta-sensitive surgical probes in U.S. Pat. No. 5,744,805 issued Apr. 28, 1998, U.S. Pat. No. 5,932,879 issued Aug. 3, 1999, and U.S. Pat. No 6,076,009 issued Jun. 13, 2000. The '805 patent discloses an ion-implanted silicon radiation detector at the tip of a probe with a preamplifier within the body of the probe connected to the detector as well as external electronics for signal handling. These devices are compared with prior art plastic scintillators which are said to have poor energy resolution. These devices are also contrasted with the use of two plastic scintillators, with one scintillator being used to correct for gamma ray contamination, described by Daghighian et al. In Med Phys. 21:153-7(1994) and U.S. Pat. No. 5,008,546 to Mazziotta et al. Such two detector devices are said to be too large for intraluminal applications. Raylman provides radiopharmaceuticals specific to diseased tissue, such as a cancerous tumor, followed by the use of a probe with one or more ion-implanted silicon detectors at its tip to locate the radiolabeled diseased tissue, the detector is preferentially responsive to beta emissions. The Raylman probes are suitable for endoscopic and minimally invasive procedures, non-invasive biopsies, and open surgical fields. Methods of providing spatial tracking of medical devices, such as ultrasound probes traversed over a patient's body, is shown in U.S. Pat. No. 6,122,538. This patent also contemplates tracking the position of a medical implement with respect to the probe. In a recent patent Wahl et al disclose the use of intravascular radiation detection probes for detection of vulnerable atherosclerotic plaque (U.S. Pat. No. 6,295,680.) In this patent they use F-18 FDG as a marker for the plaque. U.S. Pat. No. 6,167,296 to R. Shahidi describes a method and instrumentation to provide an image of internal anatomical structures which includes a position tracking system. The tracking system provides continuous, real time location and orientation of the tip of the surgical instrument with the capability of displaying images previously obtained using other imaging techniques. The Shahidi patent is directed to correlating the position of a "pointer" during surgery to the locations shown on prior tomographic images taken before surgery.

Another technique attempted to treat cancer is adoptive immunotherapy. Using lymphokines such as Interlukin-2 (IL-2) and lymphokine-activated killer cells (LAK) derived from patient peripheral blood, patients with melanoma and renal cell cancer have shown a significant positive response. A related approach is the in-vitro placement of cytokine genes into tumor specific lymphocytes. After a few days the cytokine gene supplemented, lymphocytes are delivered locally to a tumor.

Rosenberg, et al. demonstrated that a small but significant percentage of patients with melanoma and renal cell cancer could achieve a long-lasting response. (Rosenberg, et al., "Adoptive Cellular Therapy: Clinical Applications", *Biologic Therapy of Cancer*, De Vita, et al. (Eds.), J.B. Lippincott Company, Philadelphia, Pa., 1991.) A second approach to adoptive immunotherapy is to expand lymphocytes from tumors in culture. (Rosenberg, et al., "Adoptive Cellular Therapy: Clinical Applications", *Biologic Therapy of Cancer*, De Vita, et al. (Eds.), J.B. Lippincott Company, Philadelphia, Pa., (1991); Topalian, et al. "Tumor Infiltrating Lymphocytes: Evidence of Specific Immune Reactions Against Growing Cancers in Mice and Human", *Important Advances in Oncology* 1990, De Vita, et al. (Eds.), J.B. Lippincott Company, Philadelphia, Pa., p. 19 (1990), and Rosenberg, et al., "Use of Tumor-Infiltrating Lymphocytes and Interleukin-2 in the Immunotherapy of Patients with Metastatic Melanoma", *N. Engl. J. Med.*, 25: 1671, 1988.) Using these tumor-infiltrating lymphocytes (TIL), several research groups have documented superior tumor cytolytic activity and better delivery of these TIL cells to tumors than LAK cells. (Rosenberg, et al., *N. Engl. J. Med.*, id.; Dillman, et al., "Continuous Interleukin-2 and Tumor-Infiltrating Lymphocytes as Treatment of Advanced Melanoma", *Cancer*, 68: 1, 1991; Kradin, et al., "Tumor-Infiltrating Lymphocytes in Interleukin-2 in Treatment of Advanced Cancer", *Lancet*, 33: 577, 1989; and Bukowski, et al., "Clinical Results and Characterization of Tumor-Infiltrating Lymphocytes with or without Recombinant Interleukin-2 in Human Metastatic Renal Cell Carcinoma", *Cancer Res.* 51: 4199, 1991.) In general, TIL Cells appear to be therapeutically effective for patients with melanoma. Tumor-infiltrating lymphocytes have been generated from many solid tumors, including colon and breast cancer; however, these cells do not appear to mediate tumor-specific cytolytic activity in vitro and it is not known if these cells will be effective in adoptive immunotherapy models. (Rosenberg, "Gene Therapy of Cancer", *Important Advances in Oncology*, 1992, De Vita, et al. (EDS.), J.B. Lippincott Co., New York, N.Y., pp 17-18, 1992.) "Another approach to tumor therapy with tumor-specific lymphocytes is the placement of cytokine genes in cells which can deliver cytokines locally to the tumor". (Kasid, et al., "Human Gene Transfer: Characterization of Human Tumor Infiltrating Lymphocytes as Vehicles for Retroviral-Mediated Gene Transfer in Man", *Proc. Natl. Acad. Sci. USA*, 87: 473-477, 1990; and Rosenberg, et al., "Gene Transfer into Humans: Immunotherapy of Patients with Advanced Melanoma Using Tumor Infiltrating Lymphocytes Modified by Retroviral Gene Transduction", *New Engl. J. Med.*, 323: 570-578, 1990.) It has been shown in several model systems that tumor cells transfected with various, cytokine genes including IL-2, gamma interferon, and tumor necrosis factor (TNF), are more immunogenic and less tumorigenic than parent cells that do not produce cytokines. (Gansbacher, et al., "Retroviral Vector-Mediated Gamma Interferon Gene Transfer into Tumor Cells Generates Potent and Long Lasting Antitumor Immunity", *Cancer Res.* 50: 7820-7825, 1990; Gansbacher, et al., "Interleukin 2 Gene Transfer into Tumor Cells Abrogates Tumorigenecity and Induces Protective Immunity", *J. Exp. Med.*, 172: 1217-1224, 1990; and Blankenstein, et al., "Tumor Suppression after Tumor Cell-Targeted Tumor Necrosis Factor-Alpha Gene Transfer", *J. Exp. Med.* 173: 1047-1052, 1991.)

It appears that local production of cytokines near tumor cells can inhibit tumor growth and stimulate an immune response. It would therefore appear useful to find lymphocytes that recognize tumors and are capable of secreting various cytokines in response to tumors and to deliver these lymphocytes to labeled tumor cells for adoptive immunotherapy. It has been shown that certain TIL cells that secrete gamma-interferon and TNF-alpha will cause tumor regression in vivo, even though they do not display direct tumor cytotoxicity in vitro. (Barth, et al., "Interferon-Gamma and Tumor Necrosis Factor Have a Role in Tumor Regression Mediated by Murine $CD_8+$ Tumor-Infiltrating Lymphocytes", *J. Exp. Med.*, 173: 647, 1991.)

An alternative source of tumor lymphocytes is lymph nodes. Martin et al., U.S. Pat. No. 5,814,295, describes a method of locating, within cancer patients, lymph nodes enriched in tumor reactive lymphocytes so these cells can be harvested, cultured and delivered to the donor patient. The method comprises administering to the patient a radiolabeled locator (such as an antibody) which, in addition to concentration in cancer tissue, also concentrates in the lymph nodes, which are rich in tumor reactive lymphocytes. A gamma probe is then used to locate lymph nodes with increased radiation levels and those nodes are surgically excised. Nodes that appear normal (i.e. free of gross metastatic disease) but which took up the radiolabeled antibody are separated and cultured to proliferate tumor reactive cells with tumor-specific T lymphocytes therein. The cultured tumor reactive cells can then undergo gene therapy in-vitro as described above and, following a several day incubation period, transfused into the patient in accordance with adoptive immunotherapy regimes.

Gene therapy involves the insertion of genes or parts of DNA into cells or the cell membrane such that they become part of the genetic structure of the cell. Typically, a DNA vector capable of expressing a suitable gene product in the cells of the target organism is transferred into the cells of the organism, through one of a variety of processes so that it interacts with the genetic material of the cell. Prior art mechanisms for the insertion of genetic material into living tissues include direct microinjection, electroporation, (a technique in which individual cells are subjected to an electric shock to cause those cells to uptake DNA from a surrounding fluid), liposome-mediated transformation, (DNA or other genetic material is encapsulated in bilipid vesicles which have an affinity to the cell walls of target organisms), and the use of specific types of biological vectors or carriers which have the ability to transfect genetic material carried within them into specific target organisms. For example, Nemunaitis et al. reports on the beneficial effects of the direct injection into tumors in the lung of Adp 53 in combination with cisplatin (Nemunaitis, J, et al "Adenovirus-Mediated p53 Gene Transfer in Sequence with Cisplatin to Tumors of Patients with Non-Small-Cell Lung Tumor," *J. Clin.Oncology,* 18, No3, (February, 2000) pp. 609-622. Another example of the gene therapy in cardiology was performed by R. Crystal et al. (Rosengart T K, Lee L Y, Patel S R, Sanborn T A, Parikh M, Bergman G W, Hachamovitch R, Szulc M, Kligfield P D Okin P M, Hahn R T, Devereux R B, Post M R, Hackett N R, Foster T, Grasso T M, Lesser M L, Isom O W, Crystal R G. Angiogenesis gene therapy: phase I assessment of direct intramyocardial administration of an adenovirus vector expressing VEGF121 cDNA to individuals with clinically significant severe coronary disease. *Circulation* 1999; 100, pp 468-74.)

One general technique applicable to a large range of hosts is referred to as particle mediated genetic transformation. In this technique, the genetic material, (RNA or DNA) is coated onto small carrier particles. The particles are then accelerated toward target cells where the particles impact the cells and penetrate the cell walls, carrying the genetic material into the cells. At least a proportion of the cells into which the genetic material is delivered express the inserted genetic material and another smaller proportion of the cells may integrate the delivered genetic material into the cells native genetic material.

One method of accelerating coated carrier particles utilizes a larger carrier object, sometimes referred to as a macroprojectile. The carrier particles are positioned inside the macroprojectile. The macroprojectile is then accelerated at a high speed toward a stopping plate. One means of accelerating the microprojectile is to use a gunpowder driven device in which the hot gases generated by a gunpowder discharge form a hot gas shock wave, which accelerates the macroprojectile. When the macroprojectile strikes a stopping plate with a hole therein, the microprojectiles continue their travel through the hole and eventually strike the target cells. This and other acceleration techniques have been described in U.S. Pat. No. 4,945,050 issued to Sanford et al. and entitled "Method For Transporting Substances Into Living Cells And Tissues And Apparatus Therefore" incorporated by reference herein.

A second technique developed for the acceleration of carrier particles is based on a shock wave created by a high voltage electric spark discharge. This technique involves an apparatus having a pair of spaced electrodes placed in a spark discharge chamber. The high voltage discharge is then passed between the electrodes to vaporize a droplet of water placed between the electrodes. The spark discharge vaporizes the water droplet creating a pressure wave, which accelerates a carrier material previously placed in the discharge chamber. The carrier transports the particles, which are coated with the genetic materials to be delivered. The carrier is accelerated toward a retainer, where it is stopped, the particles are separated from the carrier, and the particles carried thereby pass on into the biological tissues.

This second technique has been incorporated into a handheld device that can be use for accelerating particles carrying biological materials into large whole organisms. The hand held device is described in U.S. Pat. No. 5,149,655 to an "Apparatus For Genetic Transformation". issued to McCabe et al.

A variation on the second technique for acceleration of carrier particles is based on an expanding gas shock wave, and a planar surface having carrier particles positioned on the target side of the planar surface. The shock wave that actually impacts the target area is substantially reduced when this technique is utilized. In addition, the apparatus used with this technique does not subject target cells to radiant heat or appreciable acoustic energy. Hence cell differentiation and successful cell transformation is maximized. This technique is described in U.S. Pat. No. 5,204, 253, entitled "Method and Apparatus For Introducing Biological Substances Into Living Cells." which issued to Sanford et al.

In this third technique, the delivery instrument incorporates a high pressure gas delivery system, a mechanism to generate an instantaneous gas shock out of the high pressure system, an enclosure into which the gas shock is released, contained and vented and a throat region which translates the gas shock into a particle acceleration force. The expanding gas shock is directed at, and impacts on, a back surface of the planar insertion mechanism (the carrier particles being on the front surface of the insertion mechanism). The particles are then disbursed from the front surface over a wide region of the target cells.

All of the techniques discussed, can generate only a single potentially traumatic, essentially instantaneous burst of carrier particles and thus are single shot insertion devices. In order to utilize the single shot apparatus a second time, a new carrier with genetic material thereon must be inserted into the device.

U.S. Pat. No. 5,525,510 is directed to an apparatus for injecting a continuous stream of carrier particles carrying genetic material into living cells. It includes a body member having an acceleration channel along a central axis, with the channel having an outlet at an exit end. The body also includes a source chamber connected to a compressed gas source and to the channel. Particles are placed on a carrier mounted in the body member in a position exposed to the channel so that a gas stream flowing in the channel can pick up carrier particles off of the particle carrier. A gas stream diverter is placed on the body adjacent the outlet of the channel diverts the gas stream away from the direction of flight of the carrier particles as they exit the body. In this manner a continuous stream of particles carrying genetic material can be directed to the target cells.

It has been discovered that cancer cells may have a defective gene structure. It is believed that correction of this gene structure, or modification of that structure can convert the cancerous cell to a normal cell or, as a minimum, modify or retard the cancerous characteristics of those cells and prevent the proliferation of the cancer cells. Alternatively, cancer cells can be transfected by DNA that makes them undergo the apoptosis process. Gene therapy is not limited to cancer cells, as it is believed that a gene defect can be identified in other abnormal cells. Also, genes can be delivered to the cell to cause the cell to then generate therapeutic substances.

Numerous research efforts are underway to develop methods of regenerating functional cardiac muscle in patients who have suffered myocardial infarction. A new mode of therapy for certain types of damaged tissues is direct injection of therapeutic cells into those damaged tissue. One example is the injection of stem cells or myoblast cells into ischemic or infarcted myocardium. Once cardiac muscle is damaged, it no longer has the capability to regenerate. Due to satellite cells (myoblasts), skeletal muscle cells have the capacity to differentiate into new myotubes, form new fiber and regenerate into functional muscle cells. (Yoon P D, Kao R L, Magovern G J, "Myocardial Regeneration: Transplanting Satellite Cells into Damaged Myocardium", *Texas Heart Institute Journal*. 1995; 22,2:pp119-25).

Myoblast cellular transplantation (cellular cardiomyoplasty) is a promising new treatment for those who suffer from congestive heart failure due to damaged myocardium as a result of previous infarction. In animal research studies, several investigators have demonstrated successful transplantation of autologous skeletal myoblasts into infarcted myocardium. (Atkins B Z, Lewis C W, Kraus W E, et al. "Intracardiac Transplantation of Skeletal Myoblasts Yields Two Population of Striated Cells In Situ". *Ann Thorac Surg*. 1999; 67, pp. 124-9).

Taylor and colleagues demonstrated successfully transplant of skeletal myoblast into cryoinfarcted myocardium of the same rabbits (autologous transfer). Islands of different size comprising elongated striated cells that retained characteristics of both skeletal and cardiac cells were found in the cryoinfarct. In rabbits in which myoblasts were incorporated, myocardial performance was improved. The ability to regenerate functioning muscle after autologous myoblast transplantation could have an important effect on patients after acute myocardial infarction. (Taylor D A, Atkins B Z, Hungspreugs P, et al. Regenerating Functional Myocardium: Improved Performance After Skeletal Myoblast Transplantation. *Nature Medicine*. 1998; 4,8, pp. 929-33).

During the November, 2000 American Heart Association Meeting, the research team, coordinated by professor Philippe Menasche, at Bichat Hospital in Paris reported successful cellular cardiomyoplasty in a 72 year old man undergoing open hearth surgery. (Dorozynski A, "Transplanted Cells Revive Heart Muscle", *British Medical Journal* 2000; 3211040).

A navigational system for catheter-based intramyocardial injection of drugs was designed for left ventricular guidance (Biosense™), which utilizes low-intensity magnetic field energy, and sensor tipped catheters to locate catheter position in 3-dimentional (3-D) space. Coupled with electromechanical mapping, this permits construction of a 3-D image of the left ventricle (LV), which differentiates between healthy and infarcted myocardium. (Korniowski R, Hong M K, Gepstein L. et al. Preliminary Animal Clinical Experiences Using An Electromechanical Endocardial Mapping Procedure To Distinguish Infarcted From Health Myocardium. *Circulation* 1998, 98, pp. 1116-24). This catheter-based system was integrated with a retrievable 27-gauge needle for LV intramyocardial injection. The injection site is indicated in real-time on the LV map; local electrical signals are obtained to minimize catheter-tip trauma.

The devices described herein can also localize ischemic tissues and allow the effective and accurate insertion of therapeutic genes that enable generation of new capillaries and thereby increase the blood flow and perfusion into the ischemic tissue. There are several radiolableled compounds that can be accumulated in ischemic tissue, and be localized by a radiation sensing probe. For example, cells undergoing the apoptotic process can be targeted by a radiolabeled compound called anexin-v. A radiation detection probe is used to pinpoint the schemic tissue. Genes can then be inserted into ischemic tissue causing it to generate angiogenic factor, which promotes the generation of blood vessels and increases blood perfusion.

Epstein (*New Englant Jour. Of Med.*, 340, No 2 Jan. 14, 1999, p 115-126) provides a detailed discussion of the mechanism of arterial sclerosis, atherogenesis, the genes expressed during that process and biological factors which can be addressed to treat or reverse the disease. With this knowledge one should now be able to radiolabel atherosclerotic tissue and/or plaque and then provide corrective treatment to the diseased tissue.

Coronary artery disease includes the buildup of athero plaque. While that plaque is stable and not occluding flow in a vessel, it provides little health risk. However, plaque subject to spontaneous rupture referred to as unstable or vulnerable plaque, can give rise to acute coronary thrombosis. Coronary angiography will disclose narrowed vessels but is unable to provide information regarding the nature and status of plaque in the vessel. Radiolabeled or fluorescing compounds can be used to label this vulnerable plaque. In an animal model, several radiolabeled compounds were tested for their uptake in vulnerable plaque (J. Nucl. Med. Supp. Vol. 42, 45P, May 2001). This study indicated that Tc-99m labeled Anexin-V has the highest lesion to normal ratio of radioactive uptake (due to apoptotic process in vulnerable plaque), and Tl-201 has the highest lesion to blood uptake ratio (due to neovascularization process), while F-18 labeled FDG had moderate elevated ratios of lesion to blood as well as lesion to normal uptakes (due to macrophage metabolism). Suitable fluorescing compounds are shown in the published literature and would be known to those skilled in the art. Investigation of blood vessels for unstable plaque or other lesions on its lumen is important for a variety of medical conditions such as coronary or carotid artery disease.

A sensitive and specific method of identifying these plaques and lesions is to inject the patient with a specific radiopharmaceutical or fluorescing compound. After some time (few minutes to several hours, depending on the radiopharmaceutical or fluorescing compound and the lesion) the diseased portion of the blood vessel will accumulate the radiopharmaceutical and become radioactive, or in the case of the fluorescing compound, emit an optically detectable signal. These vascular lesions can be imaged conventionally by using a large gamma camera or PET. However, the sensitivity and resolution of nuclear medicine images taken outside the human body is limited due to the intervening tissue attenuation, scatter, and the distance between the source of radioactivity and the detectors of the scanner. By bringing the detector inside the blood vessel the detection sensitivity and resolution will greatly improve. Also, it is more desirable to locate the lesion during angioplasty intra-luminally. This way it can be correlated with the conventional angiogram and appropriate therapy, such as stenting, can be applied during the same setting and procedure.

In order to localize the radiolabeled lesion inside the blood vessels, a flexible radiation detection probe is needed. A critical requirement of this flexible probe is its softness, flexibility, and thinness. This catheter-like probe can be built to include either scintillators coupled to fiberoptics or semiconductor radiation detectors.

Another disease state which is subject to labeling is cell death or damage in patients with acute myocardial infarction (heart attack). Technetium Tc-99m annexin-V can be used to radio-label these dead or damaged cells so that the location and extent of injury can be assessed. However, the only technique presently available to locate these cells is the use of large externally mounted scanning equipment (PET, Gamma Camera, etc.) U.S. Pat. No. 6,197,278 to Blankenberg et al. describes a method of imaging cell death in vivo using radiolabeled annexin. Cell death (apoptosis or necrosis) plays a crucial role in a number of homeostatic and disease processes. Tc99m linked to annexin labeled cells is detected by placing the patient within the field of a gamma camera. Alternative labeling agents are Iodine 123 or 131, Gallium 67 and Indium 111. An earlier disclosure of tissue labeling to detect ischemic infarcted tissue using Tc99m attached to a carbohydrate ligand is set forth in U.S. Pat. No. 4,952,393 to Berger et al. The patient is also scanned using an externally mounted gamma camera.

The current method of non-invasive imaging of ischemic heart tissue is by the lack of uptake of certain radiolabeled compounds in ischemic tissue. These radioactive compounds are injected intravenously into the patient and then the patient is imaged by large external gamma camera or PET scanners. The ischemic or infracted tissue takes up less of these compounds, and appear as cold spots in the nuclear medicine images. For use of gamma camera, Thalium-201 or Tc-99m labeled MIBI are used. For use with a PET scanner, N-13 labeled NH3, Rubidium, or F-18 labeled Flouro-deoxy-glucose (FDG) are used.

Although non-invasive myocardial perfusion imaging is the presently preferred method to access coronary stenosis, limitations exist in the image quality and spatial resolution as a result of signal attenuation and scatter by soft tissue located between the gamma camera or PET scanner and the myocardium being assessed.

It has been recognized that diseased cells or tissue can be radiolabeled using various cell specific, tagged compounds. It is also known that these labeled cells or labeled tissue can be located using a probe containing a radiation sensitive detector mounted to receive emissions from the radiolabeled tissue. However, no one has provided a readily usable means for locating and identifying normal or diseased tissue, delivering, in vivo, corrective treatment directly to the labeled (candidate) tissue in the patient's body while that tissue is under surveillance by the probe placed at the targeted tissue site monitoring the effective placement of the delivered treatment, and determining the effectiveness of the treatment by observing, at the treated tissue site, the biological changes to the treated tissue.

SUMMARY OF THE INVENTION

The invention comprises various embodiments of a probe for the in vivo location of radiolabeled cells or tissue using a radiation detector device, such as radiation sensitive crystals or semiconductor radiation detector materials, mounted in the tip of a tubular device insertable into a mammalian body to the region of the suspected radiolabeled tissue. Also contemplated are methods for their use. As used herein, each reference to "radiolabeled cells" is alternatively a reference to radiolabeled tissue or tissue containing radiolabeled cells Damaged tissue may pick up more radioactive material then surrounding healthy tissue. Alternatively, in some instances damaged tissue to be localized by the probe may contain less radioactive concentrations compared to the healthy tissue surrounding it. One example of this situation is radiolabeling the myocardium with a perfusion agent such as Tl-201 or a radioisotope of potassium. The ischemic myocardium will take up less of the radioactive compound than the normal myocardium. This difference in radioactive concentration is used to guide the probe to the ischemic tissue. Potassium is known to accumulate in healthy myocardium due to its adequate blood perfusion. Less accumulation occurs in ischemic tissue if the heart is under stress at the time of IV injection of potassium. No accumulation occurs in infarcted tissue. The radioisotopes of potassium, K-42 and K-43 both emit beta rays. Therefore a beta probe can be suitable for localization of the ischemic tissue using potassium radioisotopes. One problem that one encounters when probing the heart from inside the ventricles is the assurance that the probe's detector is stationary with respect to the heart tissue during the counting, which may be for a period of one or two seconds. This can be achieved by first sensing that the tip of the probe has touched the myocardium by detecting its electrophysiological signal through an electrode attached to the tip of the probe. Then as soon as contact occurs, a suction mechanism would be activated to attach the probes tip to the heart. The counting of radioactivity would then be initiated automatically for a couple of seconds. Further, the tip of the probe can have a multiple of suction ports, so that by releasing some of them and partially disengaging the probe from the heart, moving the tip by a couple of millimeters and then again fully connect it to the myocardium, the probe's tip can crawl on the ventricular wall and accurately localize the site of ischemia.

The device can also include channels therein, or associated therewith, for the placement on or in labeled tissue of compositions for modifying, in a desired manner, the radiolabeled tissue directly, the delivery of physiological fluids, or the delivery of a separate catheter mounted radiation sensitive probe, fiber optics for illumination or visualization, electrode tipped catheters for measuring or delivering electrical discharges to or from tissue surfaces, and vacuum tubes or other devices for holding the probe at a location or moving it to a second location. Alternatively, the treatment compositions are placed in the immediate vicinity of the labeled cells, while the probe is targeting the labeled cells. In one embodiment the compositions and methods provides genes for therapy. The method comprises marking abnormal cells or abnormal tissues with a radioactive tag, targeting those tagged cells using a probe directionally sensitive to the proximity of radionuclides and, through a channel placed at the site of the target cells along with the probe, delivering genetic material prepared for gene therapy treatment purposes. The probes can also be used to deliver other treatment modalities such as therapeutic cells, light for photodynamic therapy or pharmaceuticals to the labeled tissue or the area immediately surrounding the labeled tissue, i.e. the "immediate vicinity" of the radiolabeled tissue.

In addition to the application of probes to localize tissue that is a candidate for gene or cell therapy discussed above, probes incorporating features of the invention can also be used after the delivery of the therapeutic materials but before completion of the treatment procedure to determine if these delivered materials are retained in the treated tissue. This is accomplished by radiolabeling the therapeutic materials (such as radiolabeling therapeutic cells or radiolabeling the genetic materials) and then checking for its presence in the treated tissue. The radioisotope used for the labeling of the therapeutic material can be different than that used for identifying the abnormal tissue.

For example, if the localization of ischemic myocardium is desired, the patient can be I.V. injected with K-42 or K-43, both beta ray emitting isotopes of potassium. The healthy myocardium will accumulate a higher concentration of radio-labeled potassium than the ischemic tissue. A beta ray sensitive probe is then used thoracoscopically or endoventricularly to survey the myocardium and localize the ischemic tissue. Then skeletal myoblast cells, some of them labeled with a gamma emitting radioisotope (such as Tc-99m), are transplanted into the damaged myocardium. Their presence in the treated tissue can then be detected with the gamma probe.

Alternatively the probe can include mechanical, electrical-mechanical, optical, or electrical components to provide treatment to identified cells or tissue. For example, if the tagged tissue is vulnerable plaque, the probe can include an angioplasty balloon, medicated stent, or optical fibers to deliver intense light for photodynamic therapy; if the tagged tissue is a sentinel lymph node a biopsy tool can be provided; electrodes can be provided to provide ablation of tissue.

The same probe can be used to determine effectiveness of delivery of radiolabeled compounds as well as conversion to, or replacement of diseased tissue by, healthy tissue by relabeling the target site at a subsequent time and comparing the appearance of the newly labeled tissue with the prior radiation images of same tissue area.

The invention also contemplates the use of a collimating material unaffected by, or not inferring with, a magnetic field, such as a gold collimator, so the probe can be used intraoperatively within the field of an MRI diagnostic instrument.

Further, devices within the scope of the invention can include fiber optic channels, which will allow illumination and/or optical visualization of the targeted tissue at the same time a radiation image is being generated. More than one fiber optic channel will allow an image to be generated.

Still further, devices within the scope of the invention can also include position-locating means attached to the distal end of the detector. This allows the location of the detector tip within the patient's body, as well as the direction of movement of the tip, to be continuously monitored and recorded and, simultaneously, a visual image of targeted tissue to be produced and recorded along with a radiation count from the labeled tissue superimposed digitally thereon. This will provide a contemporaneous viewable image of the labeled tumor, an audible indication of radiation intensity across the targeted site, and a digital visual record of the procedure.

It should be recognized that each of these concepts, namely
  a) the labeling and location of targeted tissue,
  b) the delivery of therapy to targeted or defined tissue,
  c) the delivery of labeled treatment media (i.e. labeled therapeutic cells, genes, pharmaceuticals, etc.) to a targeted or identified tissue site in the body and determination of the correct placement of the treatment media at the desired location,
  d) subsequent to treatment, providing labeling media to the body so that effectiveness of treatment of tissue at the targeted site can be assessed in less than an hour after its delivery,
  e) use of the probe in an MRI field,
  f) mapping of the operative site, or
  g) the generation of an optical image with superposition of that image with the radiation concentration profile obtained with the intraoperative radiation detection probes or cameras may be utilized independently or two or more of these concepts may be combined in a single device or procedure.

DESCRIPTION OF THE FIGURES

FIG. 1 is cutaway side view of a first embodiment of a probe incorporating features of the invention having a central flow lumen.

FIG. 2 is cross sectional view of the first embodiment of the probe taken along line 2-2 of FIG. 1.

FIG. 3 is cross sectional view of the first embodiment of the probe taken along line 3-3 of FIG. 1.

FIG. 4 is cutaway side view of a second embodiment of a probe incorporating features of the invention having flow lumens in the wall of the probe.

FIG. 5 is cross sectional view of the second embodiment of the probe taken along line 5-5 of FIG. 4.

FIG. 6 is cross sectional view of the second embodiment of the probe taken along line 6-6 of FIG. 4.

FIG. 10 is a variation of FIG. 4 incorporating a preamplifier in the catheter tip and signal transmitter for locating the position of the tip.

FIG. 11 is a further variation of FIG. 9 showing a variable aperture.

FIG. 19 is a side view of the distal tip of the catheter of FIG. 18 in its expanded mode.

FIG. 20 is end view of the distal tip of the catheter cut along line 20-20 of FIG. 19 or 20.

FIG. 22 shows the rear surface of a scintillation crystal with a Fresnel or diffractive lens etched therein.

FIG. 23 is a schematic representation of a shaped scintillation crystal and attached light guide with a multilayer reflective coating attached thereto.

FIG. 24 is an enlarged view of the circled portion of FIG. 23

DETAILED DESCRIPTION OF THE INVENTION

Figure 7:
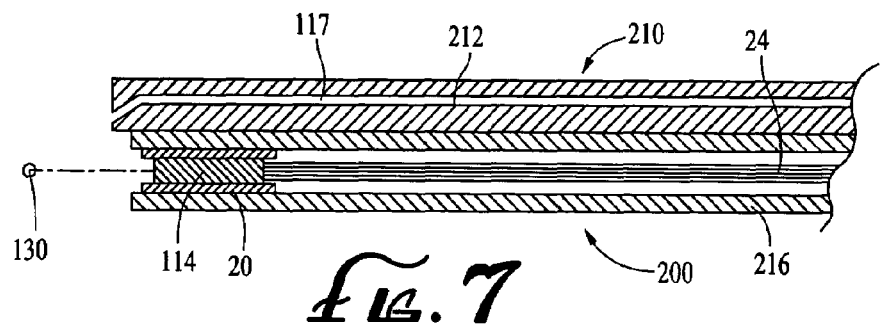
FIG. 7 is cutaway side view of a third embodiment of a probe incorporating features of the invention acting in cooperation with a separate delivery catheter.
Figure 8:
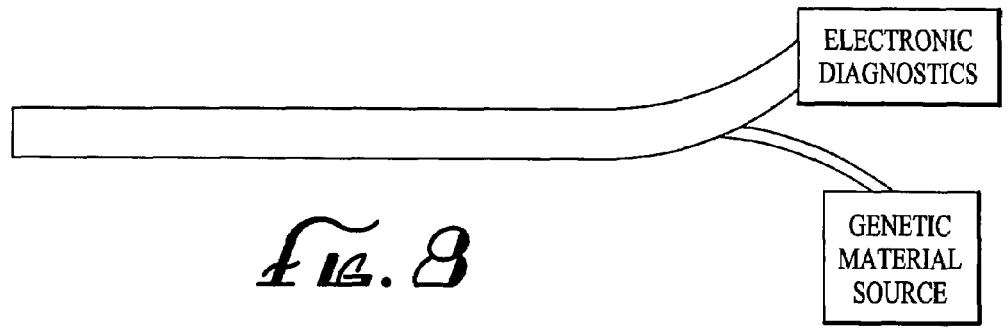
FIG. 8 is a schematic drawing showing a probe incorporating features of the invention attached to radiation indicating instrumentation and a source of genetic material for treatment purposes.

The invention comprises a body insertable probe, catheter or manually positioned device for in vivo location of radiolabeled tissue. The probe may also include means for delivery of cell altering genes, therapeutic cells, drugs, chemicals, energy or other treatment modality directly to, or to the immediate vicinity of, the radiolabeled tissue.

The intra-operative radiation probe, for the purpose of this description, may include various different device arrangements for placing radiation detection means at a particular position within the body. The probe is designed for detecting, measuring and/or localizing the radioisotope uptake of tissues within the body during a digital probe of a body orifice or minimally invasive endosurgical, interventional radiology, endovascular, or surgical procedure.

The device, in one embodiment, consists of a handheld probe unit with collimator, scintillator material(s), photomultiplier tube(s) and preamplifier circuitry; an electronics unit with a power supply plus analog and digital electronics for control, data acquisition and computer interface; and a notebook computer or embedded computer running specialized applications software for operator interface, data analysis and data display. The primary output is the count rate (counts/second), which is available as a numeric display, a color-coded graphic display, a variable frequency audible tone or clicks, and/or a numeric voice readout.

A second embodiment comprises a catheter with a radiation detector at its proximal end and signal transmission means along the catheter length from the distal to the proximal end.

A third embodiment comprises a radiation detector mounted at the tip of a finger on a surgical glove, with appropriate signal transmission means from the detector to electronic analysis equipment.

A range of software and hardware configurations is possible to address various applications including low-energy gamma, high-energy gamma and beta detection. The software provides an easily configurable Graphical User Interface (GUI) that can be readily adapted for different procedural requirements and individual user preferences.

The means for delivery of a composition to treat diseased tissue (genetic material, cells, pharmaceuticals, chemicals, etc.) may include a conduit for delivery of a liquid containing the treatment material being delivered or other delivery means known to those of ordinary skill in the art including, but not limited to, electroporation, liposomal formulations, microinjection, or the use of a gene gun or other gene delivery devices. This will allow corrective material, such as gene therapy or treatment cells, to be delivered directly to the target cells. Because the device allows direct, rather than systemic, delivery of the genetic material to the targeted cells, the concentration of the materials delivered can be increased and compounds which might negatively effect other body organs or normal tissue can be delivered with greatly reduced risk of systemic damage. A method of using the probe with therapy delivery means is also included.

Corrective cells, proteins, pharmaceuticals, chemicals, or other treatment modalities can be delivered directly to targeted tissue cells. Other means of treatment, such as ultrasound, heat, microwave energy, cryotreatment or other energy delivery means suitable to destroy targeted tissue can also be delivered directly to those cells. Alternatively, electromechanical means (rotary or reciprocal abrasion devices, ablation balloons) can be applied directly to targeted cells.

In a preferred embodiment the body insertable probe comprises a hollow tube, such as an endoscope or catheter, with one or more radiation detectors mounted at the distal end thereof. The probe includes at least one lumen from its proximal to distal end for the delivery of the genetic material to the labeled tissue located by the probe. The detector can be formed from various different materials. For example, suitable semiconductor detectors such as silicon, ion implanted silicon, cadmium telluride, or zinc cadmium telluride or scintillation crystals such as sodium iodide, mercury iodide, bismuth germanate oxide, leutitium ortho oxysilicate or, in the alternative a scintillation fluid (BC-505 or BC-519 from Bicron Corp., Newbury, Ohio) can be used. Photons generated by scintillation within the scintillator can be locally detected by, for example a photodiode (or avalanche photodiode), or transmitted through an optical guide or a bundle of optical fibers to a remotely located photo multiplier tube and then radiation at the tissue source measured and/or positionally located. The detector is located in the tip of a diagnostic catheter arranged to look forward or sidewardly by the addition of a collimating sleeve. The detector can also be designed with a hole through its center, the axis thereof being the same as an axis through the lumen down the center of the catheter. The catheter tip can be designed to articulate or bend so it can be manipulate through turns in body vessels or bent to point the detector toward particular target tissue within the body by using a guide wire through a central lumen or a lumen in the wall of the catheter. The invention also contemplates the use of a separate treatment delivery device introduced into the patient's body and maneuvered to the same target site along with the probe so that it can be separately manipulated to deliver the treatment material to the probe-located target cells, or the immediate vicinity thereof.

FIGS. 1-3 show a first embodiment of the probe 10 incorporating a lumen 12 for delivery of the treatment material to target cells. The detector 14, such as a scintillation crystal or other radiation sensing device, located within the distal end of the lumen 12 of the tube 16, has an axial bore 18 longitudinally therethrough. Within the lumen 12 is a delivery tube 13 with its wall 15 attached at one end to the detector 14 so the lumen 17 in the delivery tube 13 is contiguous with the bore 18. On the proximal end of the delivery tube 13 is a connector 28, such as those typically used on catheters or feed tubes on medical devices, for attaching to a source of a cell-altering treatment material. A liquid containing cell-altering treatment material or genetic material, which may be delivered by way of a gene gun or other gene delivery mechanism fed through the delivery tube 13 and the bore 18, can be dispensed through the lumen 12 onto target tissue directly distal to the crystal. When a detector is used for detecting beta-ray emissions from a labeled target, the portion of the tube 16 surrounding the crystal may be adequate to shield and collimate the emissions. As a result, emissions primarily distal to the probe will be sensed. However, when the target cells are labeled with radionuclides emitting gamma particles, which have a greater penetration capability, the detector or scintillation crystal must be surrounded by a collimating shield 20 so that only gamma particles emanating from a selected direction (in the case of FIG. 1, directly distal to the crystal) are seen by the crystal. The shield may be fixed in position or movable longitudlinally by a wire or pneumatics to widen or shorten the viewing window and, as a result, vary the angle of detection.

Magnetic Resonance Imaging (MRI) is a powerful anatomical imaging modality used for in vivo localization of tumors and other abnormalities in humans. While a probe or small imaging cameras can be used to locate tissue with a higher uptake of a radioactive tracer localized in vivo, these two procedures can not be used at the same time (concurrently). The problem is the interference of the MRI magnetic field with the photomultiplier tube connected to the radiation probe or the interference by paramagnetic/ferromagnetic materials used in the radiation probe, disrupting the MRI image. Lead as well as the other metals, which can disturb a magnetic field, are commonly used as collimating shields in the probes. It has been found that using non-magnetic materials, such as gold, has distinct advantages. The gold collimator will allow the probe to be used within the field of a MRI diagnostic scanner. By combining a radiation probe investigation and MR imaging concurrently, a new complementary mechanism of identifying abnormal tissues can be realized. For example, the nuclear radiation probe investigation can be done intraluminally (intracavity), laprascopically, or other forms of minimally invasive or open surgeries can be performed. Thus, surgeons can simultaneously locate tumors by MRI, and, when labeled, target cancerous tissue with the probe and treat the tissue, all being performed within a MRI unit surrounding the surgical site and without interfering with the MRI image generated.

Attached, in an optically transmitting manner, to the proximal end 22 of the crystal are optical fibers 24 which transmit photons generated by scintillation within the crystal to the proximal end of the probe 10 where they can be detected and counted by a photomultiplier assembly and electronic diagnostics. Use of long optical fibers 24 also allows location of the photomultiplier tube outside of, and a safe distance from interference by, the magnetic field. Flexible gamma and beta probes within the scope of the invention use a scintillator coupled to a distant photomultiplier tube via a long (5 to 10 foot) fiber optic light guide. All of the materials used at the tip of these probes and along the fiber optic cable are non-magnetic. For example, the collimator is made from pure gold and there is no substance in the jacket of the cable that would interfere with the MRI.

In a preferred embodiment, scintillation in the detector 14, caused by a radionuclide emitting labeled cells directly distal to the tip of the probe 10, is detected by photomultiplier diagnostic electronics 26 and an audible sound or click is generated for each detected photon or defined packet of multiple photons. The sounds or clicks are generally emitted at least every 0.1 sec such that targets with higher radio activity cause a more persistent and constant clicking. The diagnostic electronics 26 may also include computer storage capability so that a record of the probe scan can be reviewed. The storage of radiation emission levels has added value when the probe contains position sensing means as described below and shown in FIG. 10, and/or optical image generating means, that allows mapping to create an optical and radiation image of the labeled tissue. In other words, an image is generated which shows the location of the probe tip within the body along with radiation counts at that position. This image and radiation concentration can be further enhanced by providing fiber optics in the wall of the probe, which, allows illumination of the tissue being probed. Another imaging-grade optical fiber bundle or guide can be used to generate a photographic or digital image of that tissue. Using digital image manipulation techniques, the radiation counted can be imposed on the visual image.

FIGS. 4-6 show a second embodiment of the probe 100, which utilizes a solid (no central bore) scintillation crystal 114. In a manner similar to the first embodiment, the cylindrical surfaces of the crystal 100 may be covered by a shield 20. Optical fibers 24 extending proximally therefrom through a central lumen 112 are attached to diagnostic electronics 26 (not shown). This embodiment includes one or more lumens 117 within the wall of the tube 116. These lumens 117 can be used for the placement of a guide wire or steering wires typically used for placing and guiding catheters or endoscopes to a desired location. Also, one or more of these lumens may have optical fiber bundles therein for delivering illuminating light to the target site and/or obtaining a visual image of the target tissue. Alternatively, the lumens provide a channel for delivering a gene or cell therapy composition to tagged tissue located by the crystal at the distal end of the probe. As shown in FIG. 4, the lumens used to deliver the genetic material may be aimed, at the distal end of the device, to direct the delivered material to a point, i.e., a target 130, along the central axis of the crystal and a fixed distance from the distal tip of the probe. Also, while only 4 lumens are shown in the catheter wall, one skilled in the art will recognize that additional lumens may be utilized. FIGS. 5 and 6 show two lumens 117 for delivery of genetic treatment materials and two lumens 117 with an optical fiber 300 or bundle of fibers therein.

Figure 9:
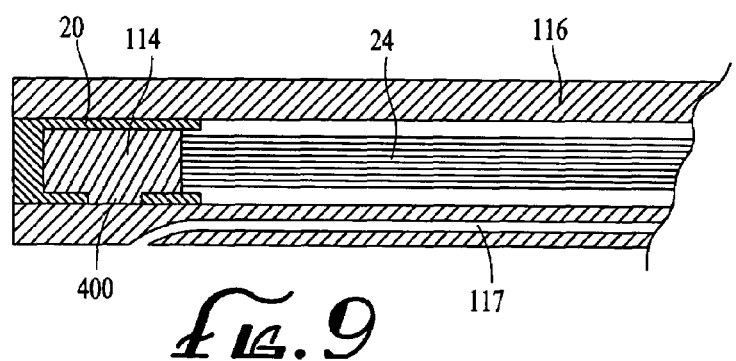
FIG. 9 is a cutaway view of a distal tip of a fourth embodiment which allows sideways viewing of radionuclide labeled cells and delivery of treatment material to those targeted cells.

FIG. 7 shows a probe 200 with the scintillation crystal 114 and fiber optics 24 in its own delivery tube 216. The gene therapy delivery catheter 210 is a separate tube with a central lumen 212. While the delivery catheter 210 is shown attached to the probe 200 to provide deliver of the gene therapy to the targeted tissue 130, one skilled in the art will recognize that the delivery catheter 210 may be placed within the body at the operative site and guided separately from the probe 200 as long as it is specifically directed to the tagged tissue located by the probe 200. FIG. 9 is a still further embodiment which includes a side viewing scintillation crystal 114 which incorporates a shield 20 with a side opening 400 and a delivery channel 117 position to deliver the genetic or cell treatment to the labeled and located tissue.

As a further modification thereof the side opening 400 can be adjustable to increase or decrease the area of the opening to allow more or less radiation received from a field of view to reach the scintillation crystal 114. FIG. 11 is a variation of FIG. 9 further including a sliding aperture shield 402, which can be moved longitudinally, or circumferentially to reduce the area of the opening. This is accomplished by moving a guide wire attached to the aperture shield 402 using mechanical, pneumatic or electronic means, such as a micromotor. FIG. 11 shows a guide wire 404 attached to the shield on one end and a translational drive means 406 on the other end. That translational drive means 406 can be, for example, a pull cord, a pneumatic drive and retraction means or a small reversable micromotor internal or external and proximal to the probe or incorporated within the probe and attached to control means. Where the aperture 18 is on the end of the probe an aperture reducing device, such as an iris located over the aperture, can be opened and closed in the same manner.

In one embodiment, the intra-operative radiation probe can include a probe design with high angular sensitivity, which is optimized for precisely locating small radiation sources. This can cause small radiation peaks to be missed by the operator during a wide-area area survey, as they move into and out of the probe's detection field too rapidly for the change in count rate to be perceived using the standard visual or audible output modes.

While each of the embodiments show a channel for delivery of a treatment material to the target cell it is contemplated that this conduit generally represents a channel for treatment delivering and can also be used for delivery of genetic treatment material in accordance with various prior art techniques such as discussed above, often referred to as a gene gun, for propelling a gene coated particle into a cell.

FIG. 10 shows a further embodiment with a shielded detector 114 in the tip of the probe connected by fiber optics 24 to a preamplifier 200, also mounted near the distal end of the probe 100. The preamplifier is then connected electrically or optically through cable 224 to diagnostic electronics 226 mounted in a location convenient to the sight and hearing of device operator.

FIG. 10 also shows position locating transmitters 210 in the wall of the distal end of the probe 100. These transmitters can, of course, be added to any of the other embodiments or replaced by detectable inserts in the distal tip. Alternatively, mechanical electrical or optical means on the proximal end of the probe can also be used to locate and track the probe tip.

In a typical use scenario, the surgeon first surveys a region, moving the probe rapidly at a distance from the tissue being examined; then performs a more intensive study of a smaller target area within the region, moving the probe more slowly and closer to the tissue being examined, to pinpoint a radiation peak more precisely. There is an inherent tradeoff in probe characteristics associated with these two modes of use. Precise localization of a small source requires that the probe has high angular sensitivity—that is, its response must be sharply peaked within a narrow solid angle. However, a narrow angular field of response may cause small sources to be missed during the initial survey phase, when the probe is moved rapidly, as they may pass into and out of the probe's detection field too rapidly to be noticed by the surgeon.

Another area of potential application is the identification (labeling) of vulnerable plaque in blood vessels. The investigation of blood vessels for unstable plaque or other lesions on its lumen is important for a variety of medical conditions such as coronary artery disease. A sensitive and specific method of identifying plaques and lesions utilizes a plaque- or lesion-specific radiopharmaceutical delivered to the patient. After some time (few minutes to several hours, depending on the radiopharmaceutical and the lesion) the diseased portion of the blood vessel will accumulate the radiopharmaceutical and emit detectable radiation. These vascular lesions can be imaged by placing the patient in the diagnostic field of a conventional, large gamma or PET camera. However, the sensitivity and resolution of nuclear medicine images taken using a scanner mounted outside the human body is limited due to the intervening tissue attenuation, scatter, and the distance between the source of radioactivity and the detectors of the scanner. By placing the detector directly inside the blood vessel at the location of the plaque or lesion, the detection sensitivity and resolution is greatly improved. It is preferred that this detector be a beta ray sensitive probe, since beta probes do not need collimators. Also, it is much more desirable to be able to locate the lesion during an intra-luminal angioplasty procedure. This way the lesion can be accurately located, its position can be correlated with the conventional angiogram and appropriate therapy, such as stenting, with or without direct delivery of treatment compositions, can be applied during the same setting and procedure.

A preferred device to locate radiolabeled lesions inside the blood vessels is a flexible catheter with one or more radiation detection probes on its distal end. This catheter-like probe can be constructed using scintillators at the distal end coupled to fiber optics, semiconductor radiation detectors connected by transmission wires to external monitoring devices or other radiation sensitive detectors.

It is further preferred that the radiation detector be as close to, or in contact with, the radiolabeled tissue in order to have the maximum sensitivity to emitted radiation. Since the diameter of the detector is less than the inner diameter of the blood vessel, there is no guarantee that the detector is in contact with the vessel's wall when the radiation counting is being done. To assure that the radiation detector(s) are brought in contact with the vessel walls, a catheter with inflatable or expandable portion at its distal end, such as an angioplasty balloon, is utilized. As described below, inflating this balloon during the radiation detection and measuring procedure ensures that the detectors are brought into contact with the labeled portion of the vessel wall.

Figure 12:
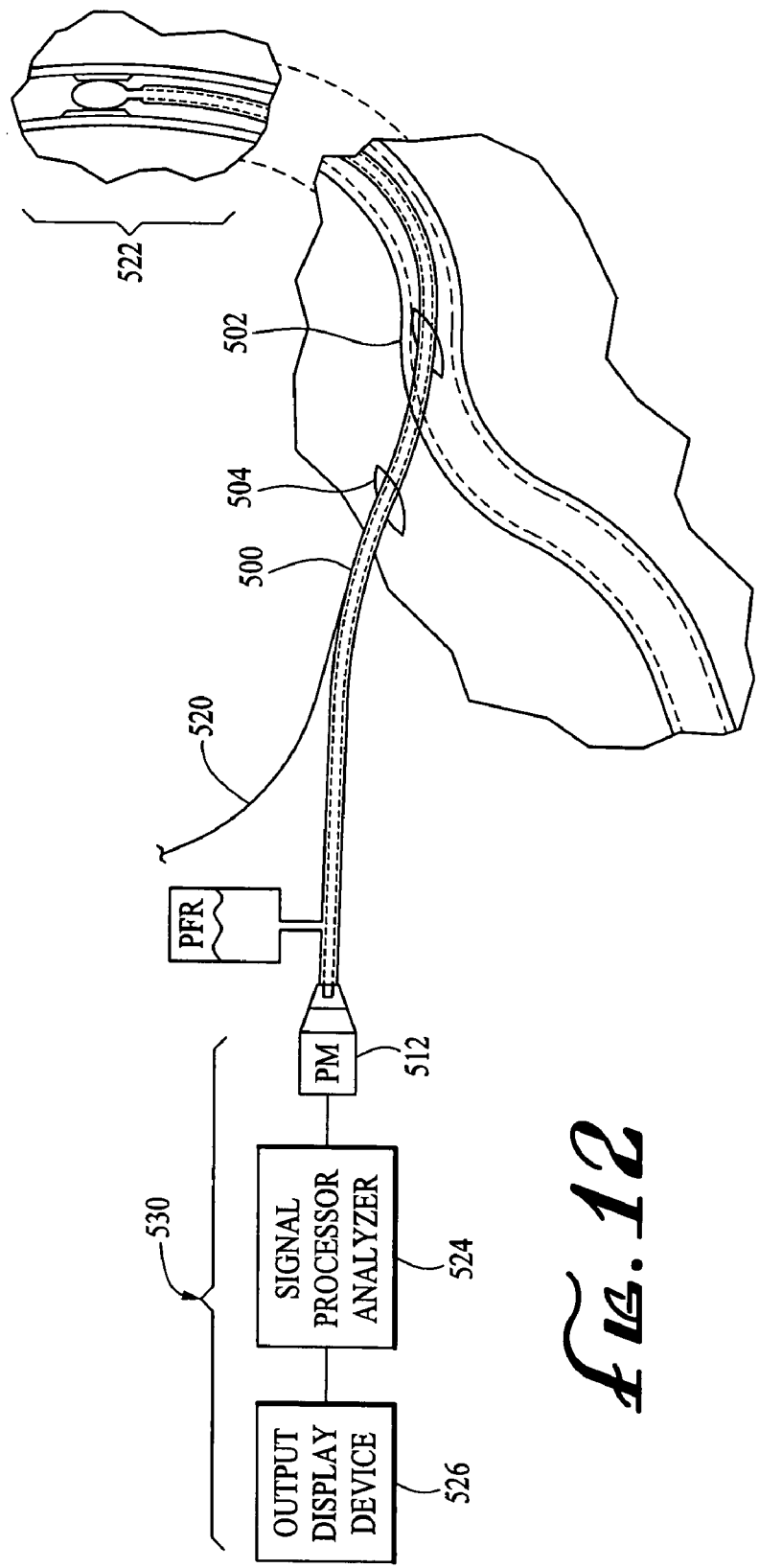
FIG. 12 is a further embodiment comprising a catheter with an inflatable balloon at its tip utilizing a scintillator liquid.
Figure 13:
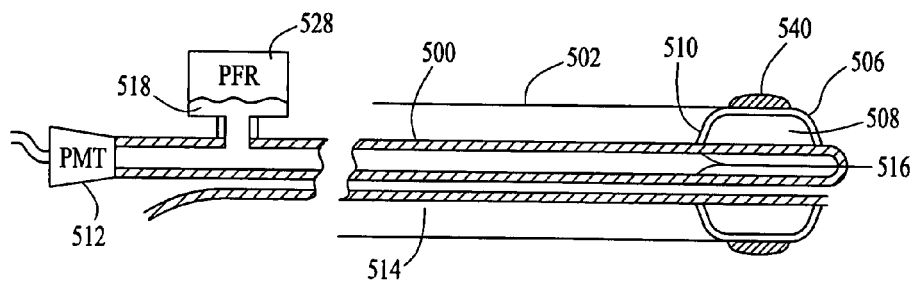
FIG. 13 is a cutaway view of the catheter of FIG. 12 with the balloon inflated to fill the vessel diameter with the inflation fluid also providing light transmission to the PMT
Figure 14:
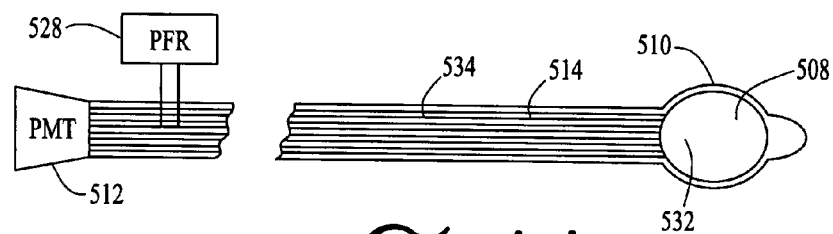
FIG. 14 is a variation of the catheter of FIG. 12 with the transmission of the scintillation light being provided by an optical fiber bundle.

A catheter 500 with a distally located radiation detection means is generally shown in FIG. 12 placed in a blood 502 vessel through a puncture site 504 in the patients skin. FIG. 13 shows a balloon 510 on the catheter tip 506 expanded to occlude the vessel 502. In the embodiment shown in FIGS. 12 and 13 a liquid scintillator 508 is use to fill and expand the balloon 510. The beta rays emitted by the labeled lesion enter the scintillation liquid 508, in the balloon 510 causing light to be emitted. That scintillation light is then transmitted to a light-sensing device (such as PMT or photosensor) 512 via a light guide or conduit 514. This light guide or conduit 514 can be a separate liquid optical guide 518 separated from the scintillator fluid by a membrane 516 as shown in FIG. 13, a fiber optic bundle or optical guide 514 as shown in FIG. 14, or a combination of liquid and fiber optics which extend the length of a lumen within the catheter tube. The catheter of FIG. 12 also includes a wire guide 520, and a lumen 538 for placement of the wire guide, so that the distal end 522 of the catheter can be steered to the desired location in the body. The proximal end of the catheter includes a photomultiplier tube (PMT) 512 operatively connected to the light channel 514, with signal processing means 524 and a display 526 attached thereto. The catheter 500 is also shown to include a pump and fluid reservoir (PFR) 528, which contains the light transmission liquid 518 or other inflation liquid. Pressurizing the light transmission fluid 518 causes the membrane 516 to move distally, pressurizing the scintillation liquid 508 and inflating the balloon 510, as shown in FIG. 13. Light generated by reaction of the radioactive emissions from radiolabeled tissue with the scintillator liquid 508 is transferred to the inflation liquid and then to diagnostic electronics 530. As shown in FIG. 14, rather than use the inflation fluid 532 to transmit the scintillation generated light, the catheter includes optical fibers (plastic, quartz, glass or other semirigid material) along its length for light transmission to the PMT 512.

Figure 15:
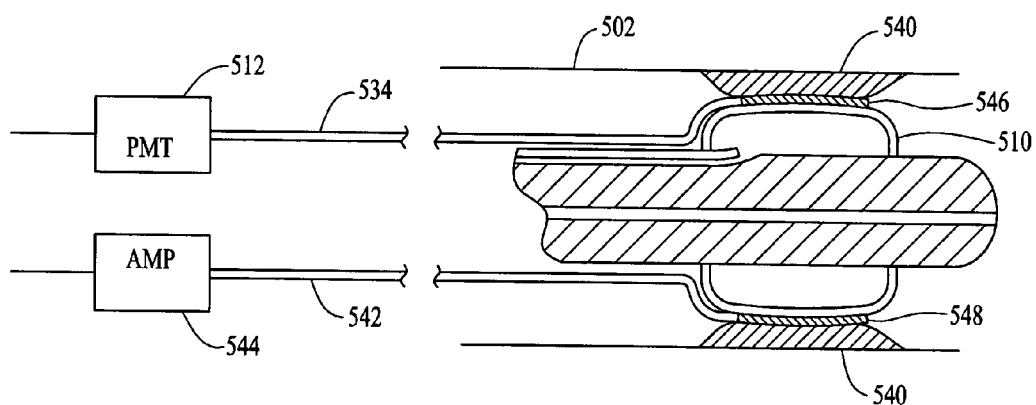
FIG. 15 is an enlarged, cutaway, side view of the distal end of a variation of the catheter of FIG. 12 with radiation detectors attached to the wall of an expanded balloon.

FIG. 15 is an enlarged cutaway side view further variation showing a cardiovascular balloon catheter 500, such as an angioplasty catheter with radiation detectors 536 attached to the outer surface of the balloon 510. Once the distal end of the catheter is positioned in the desired location in the blood vessel, i.e., adjacent suspected labeled vulnerable plaque 540 the balloon is inflated placing the detectors 536 against the plaque 540 on the vessel wall 502 so that a radiation count can be taken. In order to assure the targeted plaque 540 has been located the balloon 510 can be deflated, repositioned and re-inflated until the location with highest radiation count is located. An angioplasty procedure can then be performed, medicinal or photodynamic therapy delivered and/or a stent placed in the vessel. The radiation detector 536 is connected by an electrical lead 542 to an amplifier 544 or by an optical link 534 to a PMT. The signal is then fed to signal processing equipment 524 and a suitable display 524. While two detectors 546, 548 are shown, a single detector or multiple detectors (three or four) can be used. If a single detector is used it may be necessary to inflate the balloon multiple times alternating with rotation of the catheter between counts until the labeled plaque is optimally located. Also, both beta and gamma detectors can be used to discriminate between different tissues differently radiolabeled For illustrative purposes one scintillator 546 and one semiconductor detector 548 are shown. However, a preferred design would use multiple detectors of similar design.

Figure 16:
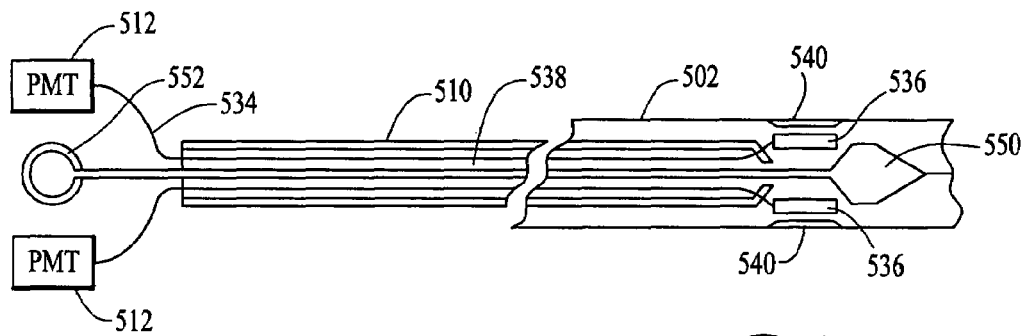
FIG. 16 is a cutaway side view of a still further version of the catheter incoporating a wedge to spread the detectors apart and against the vessel wall.
Figure 17:
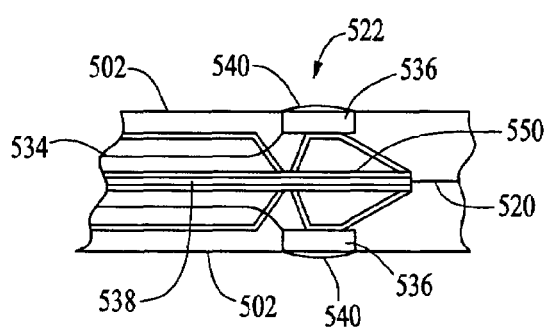
FIG. 17 is an enlarged cutaway view of distal; tip of the catheter of FIG. 16 with the detectors expanded into contact with the vessel wall.
Figure 18:
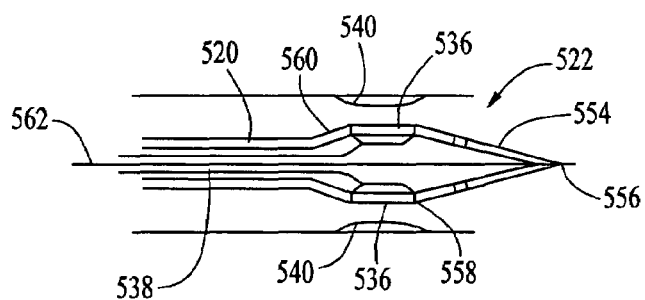
FIG. 18 is a longitudinal cutaway view of the expandable distal end of a further embodiment of a catheter including a radiation detector.

FIGS. 16 and 17 show a still further variation of a catheter tip with distal radiation detectors 536 mounted at the distal end 522 with their outer surfaces substantially in line with the catheter 500 outer wall. A retractable wedge 550 is positioned distal of the detectors 536. Pulling on the wedge handle 552 moves the wedge 550 proximally drawing it between the detectors 536 and forcing them apart and against the plaque 540 vessel 502 wall. When the wedge 550 is returned to its original position distally the detectors 536 return to their original positions clear of the vessel wall as a result of the plastic memory of the catheter 500 construction material. Alternatively, to withdraw the detectors 536 from contact with the vessel wall springs or other elastic means (not shown) may be utilized.

FIGS. 18-21 show the distal end 522 of another embodiment of a catheter 510 having radiation detectors 536 incorporated therein. The expandable portion comprises a relatively stiff, bullet shaped plastic tip 554 having a front portion 556 which tapers to a point, a central portion 558 incorporating radiation detectors 536 and a rear portion 560 between the radiation detector 536 and the catheter tube itself. The front 556, rear 560 and central portion 558 of the tip are joined by living hinges. Exposure of the central portion 558 to radiation emanating from the radiolabeled plaque 540 causes the detector 536 scintillation material to emit light or radiation sensitive semiconductor to generate an electrical output. The light is in turn collected by optical fibers 534 attached to the inner surface of radiation detector 536 on the central portion 558 and transmitted to an externally mounted PMT 512. Alternatively, small photo-sensors 548, such as avalanche photodiodes or mercuric iodide photosensors, mounted on the inner surface of the central portion of the scintillator 546 generates electrical signals which are transmitted through electrical wires 534 to an external data analysis system. In a still further alternative, the radiation detector 548 can be a semiconductor radiation detector incorporated in the central portion and the signal generated by the semiconductor from exposure to radiation transmitted to an amplifier and then to signal processors.

Figure 21:
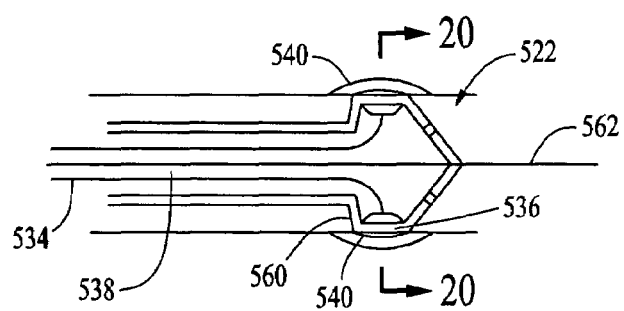
FIG. 21 is a longitudinal cutaway view of the distal tip of the catheter of FIG. 19.

The distal-most end of the tip has a opening there through to receive a guide wire 520 passing through a lumen in the catheter which is used to thread the catheter with radiation detector to the desired location in the patient's blood vessel. This opening may also be used to alternatively receive a tensioning 562 wire for use to cause the tip to expand laterally. Alternatively, the tensioning wire can be separately attached to the tip. As shown in FIGS. 19-21, when the tensioning wire 562 is pulled proximally the living hinges 564 bend, and the detectors 536 are moved into contact with the vessel 502 wall and the labeled plaque 540. The lumen 538 can also be used to deliver a treatment composition or physiological fluids so as not to interrupt blood flow through the vessel 502 upon which the probe procedure is being performed.

Figure 25:
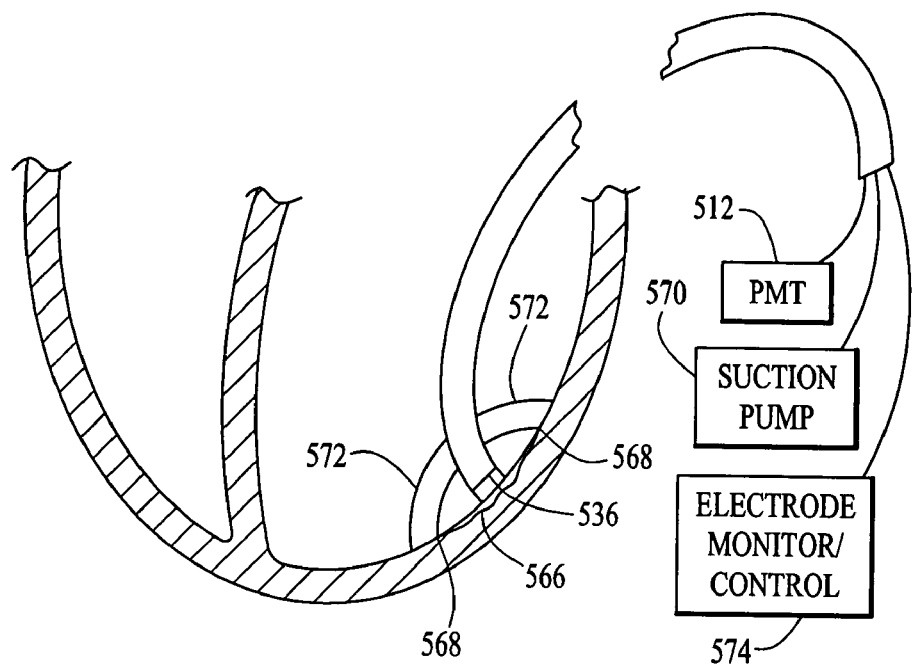
FIG. 25 is a schematic representation of a radiation sensing catheter incorporating features of the invention and which also includes electrical leads and position retaining means.

Other variations to the catheter 500 to assist in positioning and locating the catheter are shown schematically in FIG. 25 showing a catheter having features of the invention within the heart. To temporarily hold a detector 536 against targeted tissue 566, one or more vacuum delivery ports may be located at the probe surface, or in extensions 568 therefrom, with lumens connecting the vacuum ports to a source 570 of temporarily applied vacuum. These vacuum port extensions 568 can be used to hold the distal tip 522 of the catheter to targeted tissue 566 or by, alternately applying and releasing the vacuum applied to one or more vacuum extensions 568, causing the catheter's distal tip 522 to walk across a targeted tissue 566 surface. Also, electrical conduits 572 may be provided for measuring or detecting, at an external monitor 574, electrical activity from certain tissue such as myocardium or nerves to aid in positioning the catheter 500. Alternatively, these electrical conduits 572 can be used to deliver ablative electrical pulses to targeted tissue to selectively destroy tissue for treatment purposes or replaced by optical fibers to deliver intense light (such as from a laser) for treatment purposes.

A one-dimensional position sensitive silicon detector is formed by depositing layers of amorphous silicon, using low temperature plasma enhanced chemical vapor deposition (PECVD), onto a flexible plastic film, such as a polyamide coated Kapton substrate. Ion implantation is used to form a linear resistive layer of a p-type semiconductor material on the amorphous silicon. This structure can be formed on, or placed on, the surface of an elongated balloon. This balloon on the end of a catheter can then be placed in a blood vessel or other hollow body organ. By inflating the balloon, the detector is pushed into contact with the wall of the blood vessel or body organ. The position of the source of radiation impinging on the detector, in this case a beta ray, is determined by:

$$X=(Va-Vb)/(Va+Vb)$$

where Va and Vb are voltage readings taken from conductive leads attached to opposite ends of the detector.

Figure 27:
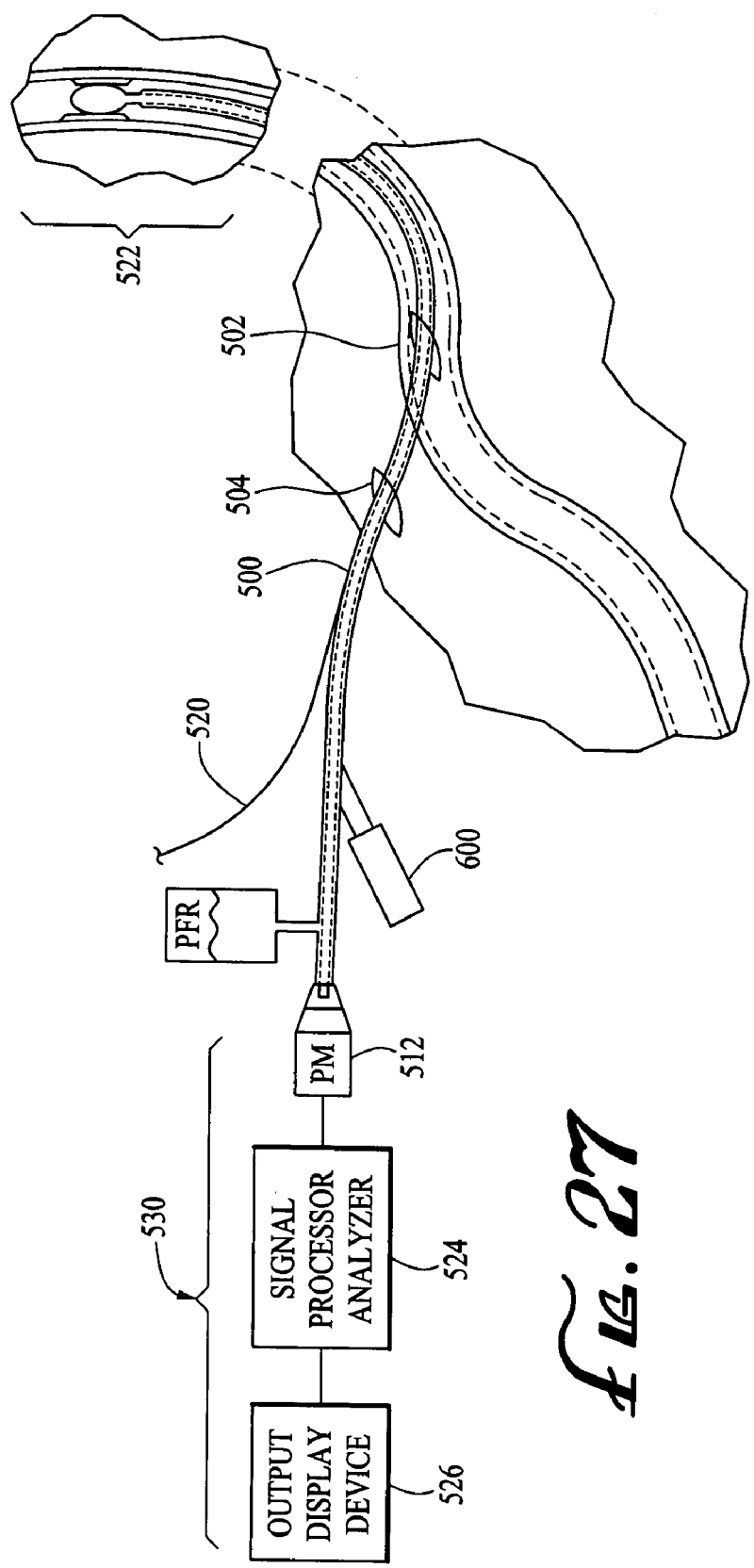
FIG. 27 is a schematic representation of a catheter with a source of light to provide photodynamic therapy through the same fiber optics as attached to the scintillation detection. The same source of light can also be used for Raman fiber amplification of scintillation light.

A factor which has limited the ability to construct catheters which are effective to detect and measure radiation from tagged cells is that the use of the very small scintillators, which are required of the small structure necessary for placement in blood vessels, results in the production of only a small amount of scintillation generated light. This light must then be transmitted to an electronic device, such as a PMT which converts that light to a measurable electrical signal. Therefore, there is a need to assure that the maximum amount of the light generated is directed toward the optical transmission means, i.e. optical fibers. In a typical arrangement, an optical conduct, light guide or multiple optical fibers are used to transfer the light generated inside the scintillator to a photo sensor (such as PMT, photodiodes, or avalanche photodiodes). The intensity of light reaching the electronic signal conversion means is lower than that generated inside the scintillator because a) some of the light is lost at the scintillator-fiber interface and b) the optical fiber attenuates the light's intensity. Newly developed Raman amplifying optical fibers can be used to compensate for the loss of scintillation light in the fiber as well as amplify the light. As shown in FIG. 27, these amplifying optical fibers require a source of light 600 to pump energy into the fiber. Resonance coupling of pumped photons and signal photons through optical fibers amplify the signal photons (Agrawal G. P. Non-Linear Fiber optics, *Academic Press* 1989; and Olson NA Noise Properties of Raman Amplifier, *J. of Lightware Technology*. Vol. 4 pp. 396-398, 1986). In this method, a light source would pump light with 100 nm or shorter wavelength into the fiber. This is done using either a ultraviolet lamp that is orthogonally coupled with the fiber optics or an ultraviolate laser that is coupled in-line. An interference filter with low in-line absorption is located on the PMT for segregation of the pumped ultraviolet light from the incoming scintillation light.

The efficacy of the scintillation crystal can be increased by providing alignment lenses and coating surfaces of optical conduits with reflective coatings so that the maximum amount of light generated is transmitted to the electronic conversion device. The lenses and coatings help to align the direction of photons exiting from the rear surface of the scintillator crystal.

Utilization of separate conventional lenses is not suitable for such applications as the diameter of the probe, which must be small (one or two millimeter) to be able to fit inside small arteries and veins, does not provide room for such an additional structure. Also using a separate lens results in an additional interface which creates further transmission losses. If no lens is used at the interface between the scintillator and fiber, the coupling efficiency is limited due to the small numerical aperture of the fiber. This leads to escape of those photons that exit the scintillator at large angles to the fiber end. Reduction of light loss at the scintillator-fiber interface is achieved by creating a Fresnel lens structure, or diffractive micro-lens structure on the rear surface of the scintillator, i.e. the surface which interfaces with the optical fiber(s). The low working distance or focal distance of these lens structures, along with the ability to fabricate these as integral parts of the scintillator medium allows for construction of miniature-radiation detection probes capable of entering relatively narrow blood vessels. These lens structures have unique capability of focusing the scintillation light at a small ratio of focal length to lens diameter; f/d<1. The result is that the path of photons exiting the rear of the scintillator crystal, particularly photons exiting at a large angle to a central axis there through, is modified to be more parallel to said central axis. Alternatively, the lens can be etched onto the end(s) of the optical guides or fibers which are mated to the rear surface of the scintillator crystal. These arrangements allow more of the light generated by scintillation to reach the PMT.

Still further, matching lenses can be formed on both the crystal and the optical fiber. Therefore, more efficient miniature and compact structures required for a flexible radiation detection probe can be constructed.

A second technique to increase efficiency is to coat all external surfaces of the components (the scintillation crystal and optical conduits), with the exception of the junction between the crystal and the optical component, with a light reflective coating which is transparent to nuclear radiation (alpha, beta, gamma radiation). This will increase internal reflection and reduce photon interaction at surfaces so that a greater percentage of light generated by scintillation reaches the crystal-optical conduit interface and a greater percentage of the light which enters the optical conduit at its input end actually reaches the output end of the conduit. This is a common procedure used on prior art scintillators and optical transmission means. However, we have discovered that use of two or more layers at least of two different refractive index coatings can provide significantly increased internal reflection with a resultant increase in the efficiency of light transmission to the external light monitoring and analysis instrumentation.

In the past, attempts have been made to improve the photon transfer efficiency of scintillators using techniques such as dome shaping, wrapping crystal with Teflon tape, painting the outer surface of the scintillator with a coating or the use of UV lens to help focus the beam from the scintillator into the PMT. Other approaches included an index matching gel and high NA (numerical aperture) UV fiber attachment to the scintillator. While all of these methods have been beneficial, they have been of limited value. In the case of incorporation of conventional lens structures, such as UV lenses, the working distance between the PMT and scintillator has to be significantly increased to compensate for the long focal distance of the lens and the source-to-object distance. In applying these techniques to probes mounted on a catheter tip, the large working/focal distance in the order of centimeters between lens/PMT/scintillators is not acceptable.

Another approach involves the use of high NA UV fiber to allow for capture of more of the scintillation light photons emitted from a scintillator. In this approach, the high NA plastic fiber is attached to the scintilltor, in an attempt to capture as much light as possible. A still further approach is to use a polycarbonate based Fresnel lens or glass Fresnel lens as an external lens to help focus the scintillation light to the PMT. This method also suffers from the high absorption coefficient at near visible light frequencies, and adds another layer of material in the path of the light with additional interfaces. Each interface between materials along the path of the transmitted light decreases the light from scintillator which reaches the PMT. Polycarbonate and glass material used to fabricate Fresnel lenses are highly absorptive at near visible frequencies therefore reducing the ability to detect low level scintillation light. All these methods also suffer from the additional problem of index matching between the scintillator and PMT and any air gap between components is further detrimental to the efficient transfer of scintillation photons the PMT.

In the present embodiment an elongated cube, cylinder, sphere shaped GSO crystal scintillator or an GSO crystal (Germanate Oxy Silicates) formed in the shape of geodesic dome is coated on all but one surface using multiple layers of alternating thin films of high and low index dielectric coatings, such as $SiO_x$, $SiN_x$ and/or organic/metal organic coatings, with each layer about 100-1000 Angstroms thick. One skilled in the art will recognize that various different crystal shapes can be utilized to focus the scintillation generated photons to a exit portion of the crystal and, in turn through a light guide to a PMT or other electronic signal conversion means while at the same time providing a crystal profile which is acceptable for small spaces such on the distal end of a catheter. For example, FIG. 23 shows a truncated pyramid shaped crystal attached to fiber optics with both the crystal and fiber optics having the described reflective coating. FIG. 24 is an enlarged view of the circled portion of FIG. 23. The multi-layer thin film coating is transparent to the nuclear radiation incident upon the scintillator due to its thinness, thereby minimizing the interaction/absorption of radiation with the multilayer coating. The coating process is performed at a temperature from about 50 to 100° C. This method can also be applied to a scintillation material formed in the shape of a sphere creating a "scintillating integrating sphere" with an exit pupil accessible for attachment of a light guide, fiberoptics, or light detector.

While scintillation materials are used to convert nuclear radiation to visible/near visible light, the efficiency of radiation to light conversion of these scintillation materials is very low, thereby requiring high sensitivity detectors such as photo-multipliers (PMT) to get a usable diagnostic reading. Because of the low efficiency of conversion, numerous mechanisms must be utilized to assure that the minimal amount of scintillation light is lost before it is detected by the PMT. The primary loss mechanism occurs inside the scintillator as some of the photons generated by scintillation do not reach the exit surface. Furthermore, where the scintillation crystals are modeled as total body photon emitters, emission efficiency of the crystal is hampered by the light emitter's "escape cone". The term "escape cone" defines the solid angle of emission from one medium of high index of refraction to one of lower index. If fiber optics are used to bring the scintillation light to a PMT, only those traveling within the acceptance cone of the fiberoptic's tip can be detected. Therefore, the fiber optics with its limited field of view is only able to detect a small fraction of scintillation light generated inside the scintillator unless that light is confined to or redirected to the acceptance cone. Beam shaping using conventional lenses or index of refraction matching between scintillator and fiber optics lead to limited improvement.

A number of major obstacles, which prevent the accurate radiation detection technique using miniature probes capable of detecting minute amounts of radiation, can be improved by use of the system modifications described herein. These include the use of an integrated micro-lens structure on the scintillator, or on the mating surface of the tip of the fiber optics, or on both, which enables the light exiting from the scintillator to be directed into the acceptance cone of the fiber optics. Collimation and focusing of the scintillation beam at a short focal distance is easily achieved using a diffractive micro-lens structure or a Fresnel lens. The fabrication of such structure is possible through commercially available techniques such as photolithography or E-beam processing. These methods do not require temperatures higher than 70° C., and do not have any adverse effects on the scintillator or fiber optics.

The integration of a highly reflective coating (90-97% reflectivity @400-450 nm) on the outside surface of the scintillator allows for the entrapment of those scintillation photons that would escape from inside the body of a scintillator modeled as a total body emitter. A thin layer of a binding film is first deposited on the scintillator's surface. Multiple layers of thin films are then applied using vapor deposition. These layers are transparent to the nuclear radiation incident upon the scintillator but reflective to most of the scintillation photons generated inside the scintillation material. As shown in FIGS. 23 and 24, multiple (eight, for example) alternating layers 606 of first and second thin film reflective materials 600, 602 are deposited on the surface of the scintillator 604. FIG. 23 shows coated scintillation crystal 604 and coated optical conduit 608 joined at interface 612. The circled portion 610 of FIG. 23 is shown enlarged in FIG. 24. These alternating layers 606, have high and low a highly reflective surface to photons with wavelengths between 400 and 450 nm, which is the range of wavelength of photons emitted by many scintillators and is the ideal wavelength range for detection by PMT. As many as 25 layers may typically be applied.

The mathematical model that describes the quarter wave plates in a multilayered stratified medium is known as the characteristic matrix of the stratified medium. A two layer, periodic structure of N-time periodicity is used. The dielectric coating applied on top of the scintillator surface is represented as two types:

Layer 1: Scintillator surface, index of refraction :n1
Layer 2: Index of refraction n2, thickness h2
Layer 3: Index of refraction n3, thickness: h3
Periodicity; N-times.

The characteristic Matrix M(h) for a two layer periodic thin film structure with one period is defined as:

$$M_2(h) = \begin{vmatrix} Cos\beta_2 * Cos\beta_3 - (P3/P2) * Sin\beta_2 * Sin\beta_3 & -i/P_3 * Cos\beta_2 * Sin\beta_3 - (i/P2)Sin\beta_2 * Cos\beta_3 \\ -iP_2 * Sin\beta_2 * Cos\beta_3 - iP2 * Cos\beta_2 Sin\beta_3 & Cos\beta_2 * Cos\beta_3 - (P2/P3) * Sin\beta_2 * Sin\beta_3 \end{vmatrix}$$

Where:

$h = h1 + h2$ $P2 = n2 \cos(\theta 2)$ $P3 = n3 \cos((\theta 3)$ $\beta_2 = (2\pi/\lambda_0) * (n_2 h_2 \cos\theta_2)$ $\beta_3 = (2\pi/\lambda_0) * (n_3 h_3 \cos\theta_3)$ While there is no limit to the number of coatings, subject to space requirements, which may be applied, once a certain number of layers are applied further layers give very limited added benefits. Each layer is typically about 100 angstrom thick. By adjusting the layer thickness and selection of the index layers within the stratified medium, a reflective surface close to 98% can be achieved. From about 6 to about 25 layers appears to be adequate. The deposition techniques are commercially available for silicate based materials. An ideal scintillator for this technique is GSO (Germanium oxy-ortho silicate). Suitable materials for the thin films comprise $SiO_x$, $SiN_x$, or various metal-organic materials.

In addition, the light guides 608 attached to the scintillator crystal 604 can also be coated with similar multiple layers of the reflective coating 606 as a means of improving the efficiency of the capture and transmission of scintillation generated light.

As stated above, the lens structure can be formed on the scintillator interface surface 612 or on a masking material deposited on the scintillator surface, with a resolution in the order of nanometers, using ion or electron beam etching. As a second alternative photochemical or optical lithography can be used to form a lens structure on the scintillator chip with a resolution in the order of 0.1 micron. FIG. 21 shows the rear surface (i.e. the interface surface 612) of a cylindrical scintillation crystal with a Fresnel lens 614 etched therein. If the lens is formed on the end of the optical guide, it has the same appearance as in FIG. 22. This will serve to focus the scintillation light to optic fibers for transmission to a PMT with increased efficiency.

Figure 26:
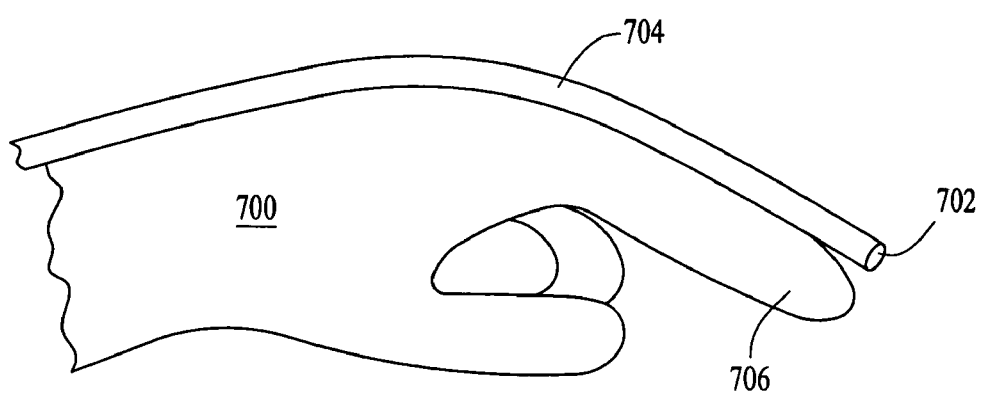
FIG. 26 is a side view of a glove mounted probe.

A still further embodiment, shown in FIG. 26 is a surgical glove 700 with the distal end 702 of a radiation detection probe 704 located at, and secured to, the tip of a finger 706 of the glove 700. When worn by an individual, the finger mounted probe 704 can be directed to radiolabeled tissue. Any of the various embodiments described above can be incorporated as the detection probe 704 in the glove embodiment.

To use any of the embodiments disclosed herein, or any variations thereof that one skilled in the art, based on the teaching herein, could adopt, the following procedure would be used:
1) A radionuclide labeled, tissue specific material is delivered to a patient, generally systemically, and the labeling material is allowed to circulate through the patients body until the material concentrates at intended target tissue, resulting in radiolabeled (tagged) tissue;
2) The target sites are generally located by techniques known to diagnosticians (palpation, digital probing, nuclear scanning devices, cat scans, MRI, etc);
3) A probe incorporating features of the invention is placed in the vicinity of the previously radiolabeled tissue, by known techniques such as those for delivery of catheters or endoscopes to desired locations or less invasive surgical techniques. Alternatively, the exposed tissue in an open surgical site can be scanned with the tip of the probe or glove mounted probe. X-ray or a CAT, MRI, or ultrasound scanner can also be used to guide the probe to the desired location.
4) Once radiolabeled tissue is located by the probe, as indicated by an audible signal or image delivered by the electronic diagnostics attached to the proximal end of the probe, treatment material prepared for treatment purposes is delivered directly to the targeted/tagged cells using the probe to assure delivery to the vicinity of the targeted cells. Alternatively, a treatment procedure, such as angioplasty or tissue ablation is performed.
5) If the treatment composition, such as therapeutic cells or genetic material, is also radiolabeled with a radioisotope different than the one used to locate the diseased tissue, the efficacy of delivery to the target site can be determined using a probe tuned to the radiation of the second radioisotope A further embodiment contemplated by the invention is the use of the above-described radio-detecting probe to map targeted tissue. In this embodiment the probe is mechanically, optically, electronically, or electromagnetically connected to an x-y-z coordinate generating system which allows the position of the tip of the probe within the patient at the site of targeted tissue to be continuously identified and recorded and that position to be coordinated with the level of radiation emanating from a target located by the detector in the tip of the probe. As a result, the probe can be moved at a preset distance from target tissue, up and down as well as across the target tissue in multiple parallel paths to generate an image of the level of radioactive emissions from that tissue, showing portions thereof which have greater concentrations of the labeling compound.

The prior art, such as U.S. Pat. Nos. 5,042,486 and 5,899,860 to Pfeifer, et al. and U.S. Pat No. 5,776,064 disclose the location of the catheter tip using a) a nonionizing field, such as an electromagnetic or acoustic field, and/or receiving and transmitting antennas attached to the patient or b) a catheter mounted emitter with three receivers mounted on or surrounding the patient. FIG. 10 shows such transmitters 210 located in the probe tip. However, the invention contemplates the use of numerous other techniques to track and locate the probe tip, known to those skilled in the art.

Once the tip position is known, that position can be coordinated with the radiation reading there obtained, recorded and/or indicated by the photomultiplier diagnostic electronics 26. Also the inclusion of the position identifying transmitters 210 is not limited to the embodiment of FIG. 10 but can be incorporated in any of the other embodiments described and/or shown.

One skilled in the art will also recognize that the detector or scintillation crystal, while shown as a single detector, may in fact be multiple detectors, or an array of detectors, or a continuous film of detectors which are individually sensed or multiplexed.

It is evident from the foregoing that there are many additional embodiments of the present invention which, while not expressly described herein, are within the scope of this invention and may suggest themselves to one of ordinary skill in the art. For example, the invention contemplates the use in place of the scintillation crystal, of multiple detectors, arrays of detectors, and continuous sheet of detector material capable as well semiconductor detectors, position sensitive semiconductor detectors and their arrays. It is also contemplated that beta or gamma cameras as well as optical cameras can be mounted within the probe at or near the distal tip to receive signals from labeled tissue and then transmit those signals electrically, optically or buy other known transmission means to equipment external of the probe to allow real time visualization of regions within the patients body which are being detected by the probe tip.

We claim:
1. A catheter for in vivo detection of nuclear or fluorescent radiation emitted from tagged biological tissue within a human body comprising: an elongated tube having at least one lumen, the lumen extending from a distal end of the tube, for positioning within the human body and a length sufficient such that, in use, a proximal end of the tube is external to the human body, an expandable portion located on the distal end of said tube, drive means for causing the expandable portion to increase in diameter being operatively connected to the expandable portion, control means for the drive means being located at the proximal end of the tube, at least one radiation detector mounted on or in the expandable portion, a signal conduit positioned in said at least one lumen, said signal conduit connected at a first end to the at least one radiation detector and at a second end to diagnostic instrumentation external of the human body wherein the radiation detector is a scintillator, the signal conduit is an optical transmitting liquid that is operatively connected to an external photo multiplier tube or a photosensor, the photo multiplier tube or a photo sensor in turn connected to a signal processor.

2. The catheter of claim 1 wherein the expandable portion located on the distal end is an inflatable balloon.

3. The catheter of claim 2 wherein the drive means to expand the inflatable balloon comprises a controlled quantity of the optical liquid delivered through one of the lumens to the inside of the balloon said optical liquid being noncompressible.

4. The catheter of claim 2 wherein the inflatable balloon is filled with a scintillation liquid, the scintillation liquid being retained in the balloon by an expandable, optically transparent membrane separating the scintillation liquid from the distal end of an inflation lumen extending through the length of the tube, the balloon being inflated by delivering a controlled quantity of a non-compressible liquid through the inflation lumen causing the membrane to expand into the balloon and inflating the balloon, the non-compressible liquid being an optical transmitting fluid.

5. The catheter of claim 1 having a second lumen for delivery of a therapeutic material to the tagged biological tissue or to tissue adjacent to the tagged biological tissue.

6. The catheter of claim 1 also having a position locating means on the distal end thereof for sensing the position of said distal end within the human body using an externally mounted position sensing detector.

7. The catheter of claim 6 wherein said externally mounted position sensing detector comprises magnetic field sensing micro coils which detect the location of the position locating means on the catheter.

8. A catheter for in vivo detection of nuclear or fluorescent radiation emitted from tagged biological tissue within a human body comprising: an elongated tube having at least one lumen, the lumen extending from a distal end of the tube, for positioning within the human body and a length sufficient such that, in use, a proximal end of the tube is external to the human body, an expandable portion located on the distal end of said tube, drive means for causing the expandable portion to increase in diameter being operatively connected to the expandable portion, control means for the drive means being located at the proximal end of the tube, at least one radiation detector mounted on or in the expandable portion, a signal conduit positioned in said at least one lumen, said signal conduit connected at a first end to the at least one radiation detector and at a second end to diagnostic instrumentation external of the human body wherein the expandable portion located on the distal end comprises a tubular extension hinged at a first end to the distal end of the tube, the tubular extension comprising two or more elongated pieces capable of being moved radially outward from a central axis along the length of the tube and being returned to their original position, each elongated piece canying a radiation detector in a central part thereof.

9. The catheter of claim 8 wherein each elongated piece is joined at a second end to the elongated pieces adjacent thereto, the drive means comprising a pull wire having a proximal end extending from the proximal end of the tube and a distal end attached to the elongated pieces at their second end, such that applying a pulling motion to the proximal end of the pull wire causes the central part of each elongated piece to move outward from the central axis and releasing the pull wire allows them to return to their prior position.

10. The catheter of claim 8 the drive means comprising a wedge on the distal end of a pull wire, the pull wire having a proximal end extending from the proximal end of the tube such that applying a pulling motion to the proximal end of the pull wire causes the wedge to move proximally to a point between a central part of each elongated piece, moving each elongated piece outwardly from the central axis, and returning the wedge to its original position allows the elongated pieces to return to their prior position.

11. A catheter for in vivo detection of nuclear radiation emitted from tagged biological tissue within a human body comprising:
   an elongated tube having at least one lumen extending from a distal end of the tube for positioned within the human body and a length sufficient such that, in use, a proximal end of the tube is external to the human body,
   a detector portion located on the distal end of said tube,
   at least one scintillation radiation detector comprising a scintillation material mounted on or in the detector portion,
   a light transmission conduit positioned in said at least one lumen, said light transmission conduit connected at a first end to the at least one scintillation radiation detector and at a second end to diagnostic instrumentation external of the human body,
   wherein the at least one scintillation radiation detector includes an integral microlens formed on a surface at an interface between the scintillation detector and the light transmission conduit connected to the radiation detector said integral micro lens functioning to focus scintillation light generated into the light transmission conduit.

12. The catheter of claim 11 wherein the integral microlens is formed on a surface of the scintillation material to which the light transmission conduit is joined.

13. The catheter of claim 12 wherein the integral microlens is a diffractive lens.

14. The catheter of claim 12 herein the integral microlens is a Fresnel lens.

15. The catheter of claim 11 wherein the integral microlens is formed on a surface of the light transmission conduit to which the scintillation material is joined.

16. The catheter of claim 11 wherein the integral microlens is formed on both a surface of the light transmission conduit and on a surface of the scintillation material where the light transmission conduit and scintillation material are joined.

17. The catheter of claim 11 wherein the light transmission conduit is an optical fiber or optical transmitting fluid and scintillation light generated by the scintillation material is amplified in the optical fiber by pumping ultraviolet light into the fiber using an external source of light, the ultraviolet light being filtered from entering an external PMT while allowing the scintillation light to enter the external PMT.

18. The catheter of claim 11 wherein the light transmission conduit is an optical fiber or optical transmitting fluid and a source of light is used to deliver therapeutic light to diseased tissue or vulnerable plaque, for the purpose of photodynamic therapy or ablation, through said optical fiber, said optical fiber also providing transmission to the diagnostic instrumentation of scintillation light generated by the scintillation material.

19. A catheter for in vivo detection of nuclear or fluorescent radiation emitted from tagged biological tissue within a human body comprising: an elongated tube having at least one lumen, the lumen extending from a distal end of the tube, for positioning within the human body and a length sufficient such that, in use, a proximal end of the tube is external to the human body, an expandable portion located on the distal end of said tube, drive means for causing the expandable portion to increase in diameter being operatively connected to the expandable portion, control means for the drive means being located at the proximal end of the tube, at least one radiation detector mounted on or in the expandable portion, a signal conduit positioned in said at least one lumen, said signal conduit connected at a first end to the at least one radiation detector and at a second end to diagnostic instrumentation external of the human body, wherein the at least one radiation detector is a scintillation detector and the signal conduit is a light transmitting conduit and the signal conduit is an optical fiber or optical transmitting fluid and scintillation light from the scintillation detector is amplified in the optical fiber by pumping ultraviolet light into the fiber using an external source of light, the ultraviolet light being filtered from entering the PMT while allowing the scintillation light to enter.

20. A catheter for in vivo detection of nuclear or fluorescent radiation emitted from tagged biological tissue within a human body comprising: an elongated tube having at least one lumen, the lumen extending from a distal end of the tube, for positioning within the human body and a length sufficient such that, in use, a proximal end of the tube is external to the human body, an expandable portion located on the distal end of said tube, drive means for causing the expandable portion to increase in diameter being operatively connected to the expandable portion, control means for the drive means being located at the proximal end of the tube, at least one radiation detector mounted on or in the expandable portion, a signal conduit positioned in said at least one lumen, said signal conduit connected at a first end to the at least one radiation detector and at a second end to diagnostic instrumentation external of the human body, wherein the at least one radiation detector is a scintillation detector and the signal conduit is a light transmitting conduit and the signal conduit is an optical fiber or optical transmitting fluid and a source of light is used to deliver therapeutic light to diseased tissue or vulnerable plaque, for the purpose of photodynamic therapy or ablation, through said optical fiber, said optical fiber also providing transmission of the scintillation light from the scintillation detector to the diagnostic instrumentation.

* * * * *

UNITED STATES PATENT AND TRADEMARK OFFICE
CERTIFICATE OF CORRECTION

PATENT NO.         : 7,373,197 B2
APPLICATION NO. : 10/190113
DATED              : May 13, 2008
INVENTOR(S)        : Farhad Daghighian and Henry M. Daghighian It is certified that error appears in the above-identified patent and that said Letters Patent is hereby corrected as shown below:

- Column 29, Claim 8, Line 36, is written as: "to their original position, each elongated piece canying a". It should read as: "to their original position, each elongated piece carrying a".

Signed and Sealed this

Tenth Day of November, 2009

David J. Kappos
*Director of the United States Patent and Trademark Office*